United States Patent
Bruhlmann et al.

(10) Patent No.: US 11,566,062 B2
(45) Date of Patent: Jan. 31, 2023

(54) METHODS FOR MODULATING PROTEIN MANNOSYLATION PROFILES USING MADURAMYCIN, NARASIN, OR SALINOMYCIN

(71) Applicant: ARES TRADING S.A., Aubonne (CH)

(72) Inventors: David Bruhlmann, Lausanne (CH); Thomas Vuillemin, Corsier-sur-Vevey (CH); Martin Jordan, Ecublens (CH); Hervé Broly, Chatel-St Denis (CH)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 16/954,544

(22) PCT Filed: Dec. 19, 2018

(86) PCT No.: PCT/EP2018/085909
§ 371 (c)(1),
(2) Date: Jun. 17, 2020

(87) PCT Pub. No.: WO2019/121961
PCT Pub. Date: Jun. 27, 2019

(65) Prior Publication Data
US 2020/0339665 A1 Oct. 29, 2020

(30) Foreign Application Priority Data
Dec. 20, 2017 (EP) .................... 17209007

(51) Int. Cl.
*C07K 16/00* (2006.01)
*A61K 39/00* (2006.01)

(52) U.S. Cl.
CPC .............. *C07K 16/00* (2013.01); *A61K 39/00* (2013.01); *C07K 2317/20* (2013.01); *C07K 2319/00* (2013.01)

(58) Field of Classification Search
CPC .... A61K 39/00; C07K 16/00; C07K 2317/20; C07K 2317/41; C07K 2319/00; C12P 21/005
See application file for complete search history.

(56) References Cited

FOREIGN PATENT DOCUMENTS

| WO | WO 2014/151878 | 9/2014 |
|----|----------------|--------|
| WO | WO 2015/066357 | 5/2015 |

OTHER PUBLICATIONS

Joanna Stefańska, Activity of Natural Polyether Ionophores: Monensin and Salinomycin against Clinical *Staphylococcus epidermidis* Strains, Polish Journal of Microbiology 2015, vol. 64, No. 3, 273-278.*
Written Opinion in International Application No. PCT/EP2018/085909, dated Jun. 17, 2019, pp. 1-17.

* cited by examiner

*Primary Examiner* — Julie Ha
*Assistant Examiner* — Erinne R Dabkowski
(74) *Attorney, Agent, or Firm* — Saliwanchik, Lloyd & Eisenschenk

(57) ABSTRACT

The present invention relates to methods and compositions for modulating mannosylation profile of recombinant proteins expressed by mammalian host cells during the cell culture process, using a polyether ionophore.

10 Claims, 13 Drawing Sheets

METHODS FOR MODULATING PROTEIN MANNOSYLATION PROFILES USING MADURAMYCIN, NARASIN, OR SALINOMYCIN

CROSS-REFERENCE TO RELATED APPLICATION

This application is the U.S. national stage application of International Patent Application No. PCT/EP2018/085909, filed Dec. 19, 2018.

FIELD OF THE INVENTION

The present invention relates to methods and compositions for modulating mannosylation profile of recombinant proteins expressed by mammalian host cells during the cell culture process, using a polyether ionophore.

BACKGROUND OF THE INVENTION

The glycosylation profile of a protein, such as a therapeutic protein or an antibody, is an important characteristic that influences biological activity of the protein through changes in half-life and affinity due to effects for instance on folding, stability and antibody-dependent cellular cytotoxicity (ADCC, one of the mechanism responsible for the therapeutic effect of antibodies)(Eon-Duval et al., 2012). Glycosylation is highly dependent on the cell line that is used for the production of the protein of interest, as well as on the cell culture processes (pH, temperature, cell culture media composition, raw material lot-to-lot variation, medium filtration material, air, etc.).

ADCC activity is influenced by the amount of fucose and/or mannose linked to the oligosaccharides of the Fc region, with enhanced activity seen with a reduction in fucose and/or an increase in mannose. Indeed, for instance, compared to fucosylated IgGs, non-fucosylated forms exhibit dramatically enhanced ADCC due to the enhancement of FcγRIIIa binding capacity without any detectable change in complement-dependent cytotoxicity (CDC) or antigen binding capability (Yamane-Ohnuki and Satoh, 2009). Similarly, antibodies exhibiting high level of mannose-5 glycans also presented higher ADCC (Yu et al., 2012). Thus, where the ADCC response is the principle therapeutic mechanism of antibody activity, the provision of methods for the preparation of recombinant therapeutic protein with a glycosylation profile characterized by decreased fucosylation and/or increased mannosylation, are beneficial. The advantages of highly mannosylated antibodies also include achieving therapeutic efficacy at low doses.

Modulation of protein glycosylation, such as mannosylation, is of particular relevance for marketed therapeutic proteins or antibodies as glycosylation (such as mannosylation) can impact therapeutic utility and safety. Further, in the frame of biosimilar compounds, control of the glycosylation profile of a recombinant protein is crucial, as the glycosylation profile of said recombinant protein has to be comparable to the glycosylation profile of the reference product. Some compounds have been reported as having an impact on mannosylation of proteins produced recombinantly: for instance, WO2014151878 and WO2014159259 disclose the use of oligosaccharides such as sucrose to increase mannosylation levels, WO2015105609 relates to the use of arginase inhibitor and WO2015066357 suggests the use of monensine.

However, there still remain a need for culture conditions and production methods that allow controlling the glycosylation profile, such as mannosylation profiles, of a recombinant protein, while not impacting the performance of the cells in culture or the recombinant protein yield. The present invention addresses this need by providing methods and compositions for modulating recombinant protein glycosylation, such as recombinant protein mannosylation, while keeping acceptable production yield/conditions.

SUMMARY OF THE INVENTION

In one aspect the invention provides a method of producing a recombinant protein with a modulated mannosylation profile, said method comprising culturing a host cell expressing said protein in cell culture medium comprising a polyether ionophore.

Alternatively, here is disclosed a method of producing a recombinant protein with a modulated mannosylation profile, said method comprising culturing a host cell expressing said protein in cell culture medium complemented with at least one feed comprising a polyether ionophore.

In a further aspect, the invention provides a composition comprising a cell culture medium comprising a polyether ionophore or supplemented with a polyether ionophore.

In another aspect, the invention provides a pharmaceutical composition comprising the recombinant protein with a modulated mannosylation profile produced by the methods of the invention and a pharmaceutically acceptable carrier.

In another aspect, the invention provides a composition comprising a recombinant protein with a modulated mannosylation profile produced by the methods of the invention.

In a further aspect, the invention provides use of a polyether ionophore in a cell culture medium or in a feed medium for modulating the mannosylation profile of recombinant proteins.

The polyether ionophore is preferably selected from the group consisting of maduramycin, narasin or salinomycin.

BRIEF DESCRIPTION OF THE FIGURES

Notes: In all the figures: SO followed by a concentration=concentration of salinomycin at the start of the culture, NO followed by a concentration=concentration of narasin at the start of the culture, MO followed by a concentration=concentration of maduramycin at the start of the culture, M5 followed by a concentration=concentration of maduramycin added at day 5 as a feed, M7 followed by a concentration=concentration of maduramycin added at day 7 as a feed. uM=micromolar. mioVCs/mL=million viable cells per mL.

DETAILED DESCRIPTION OF THE INVENTION

Figure 1:
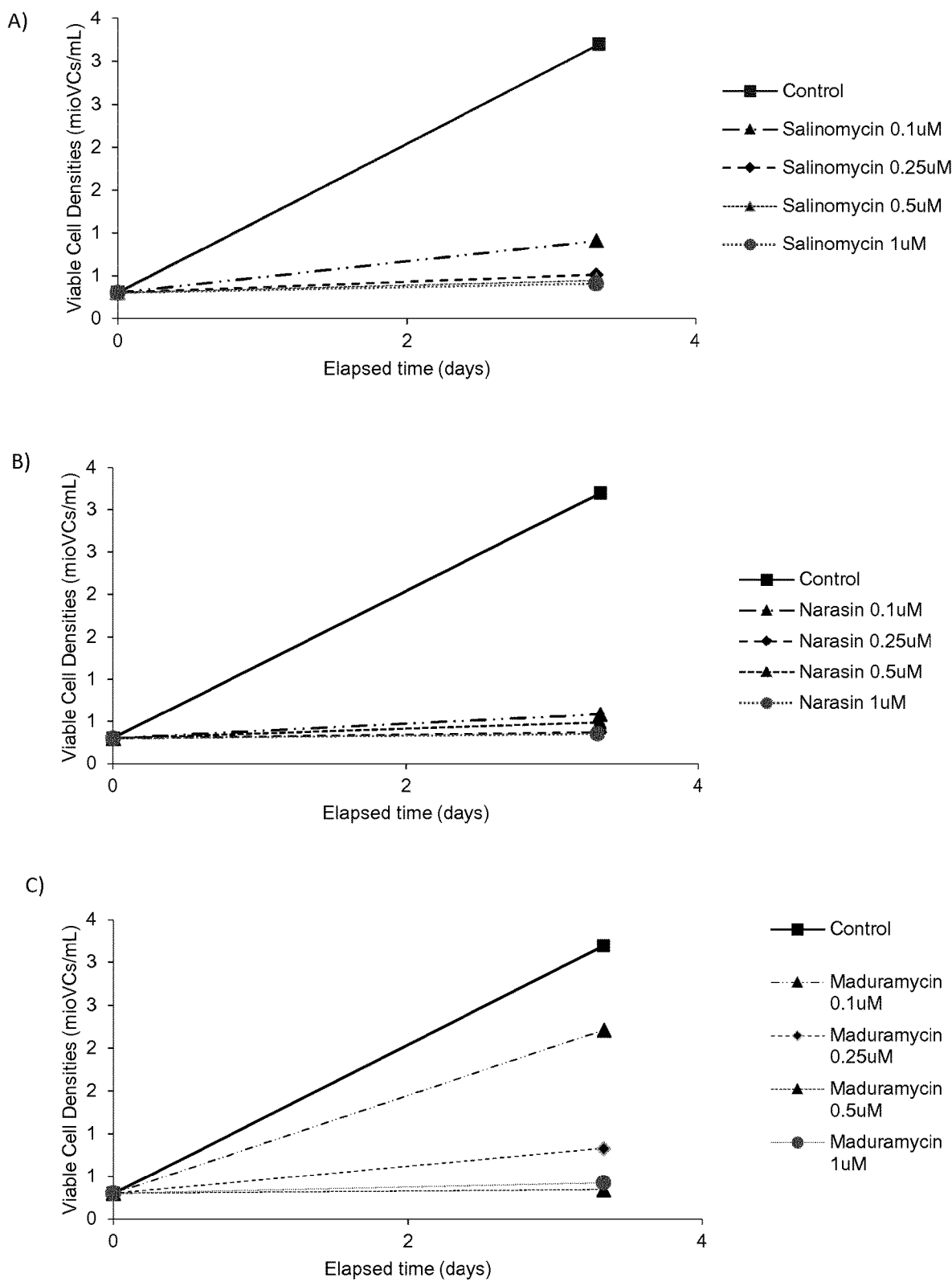
FIG. 1 shows density of viable cells (ViCell®) in relation to time for mAb1 cells cultured at different polyether ionophores concentrations in minibioreactor Ambr.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "and/or" used in a phrase such as "A and/or B" herein is intended to include "A and B", "A or B", "A", and "B".

The term "cell culture" or "culture" is meant the growth and propagation of cells in vitro, i.e. outside of an organism or tissue. Suitable culture conditions for mammalian cells are known in the art, such as taught in Cell Culture Technology for Pharmaceutical and Cell-Based Therapies (2005). Mammalian cells may be cultured in suspension or while attached to a solid substrate.

The terms "cell culture medium," "culture medium", "medium," and any plural thereof, refer to any medium in which cells of any type can be cultured. A "basal medium" refers to a cell culture medium that contains all of the essential ingredients useful for cell metabolism. This includes for instance amino acids, lipids, carbon source, vitamins and mineral salts. DMEM (Dulbeccos' Modified Eagles Medium), RPMI (Roswell Park Memorial Institute Medium) or medium F12 (Ham's F12 medium) are examples of commercially available basal media. Alternatively, said basal medium can be a proprietary medium fully developed in-house, also herein called "chemically defined medium" or "chemically defined culture medium", in which all of the components can be described in terms of the chemical formulas and are present in known concentrations. The culture medium can be free of proteins and/or free of serum, and can be supplemented by any additional compound(s) such as amino acids, salts, sugars, vitamins, hormones, growth factors, depending on the needs of the cells in culture.

The term "feed medium" or "feed" (and plural thereof) refers to a medium used as a supplementation during culture to replenish the nutrients which are consumed. The feed medium can be a commercially available feed medium or a proprietary feed medium (herein alternatively chemically defined feed medium).

The term "bioreactor" or "culture system" refers to any system in which cells can be cultured, preferably in batch or fed-batch mode. This term includes but is not limited to flasks, static flasks, spinner flasks, tubes, shake tubes, shake bottles, wave bags, minibioreactors, bioreactors, fibre bioreactors, fluidized bed bioreactors, and stirred-tank bioreactors with or without microcarriers. Alternatively, the term "culture system" also includes microtiter plates, capillaries or multi-well plates. Any size of bioreactor can be used, for instance from 0.1 millilitre (0.1 mL, very small scale) to 20000 litres (20000 L or 20 KL, large scale), such as 0.1 mL, 0.5 mL 1 mL, 5 mL, 0.01 L, 0.1 L, 1 L, 2 L, 5 L, 10 L, 50 L, 100 L, 500 L, 1000 L (or 1 KL), 2000 L (or 2 KL), 5000 L (or 5 KL), 10000 L (or 10 KL), 15000 L (or 15 KL) or 20000 L (20 KL).

The term "fed-batch culture" refers to a method of growing cells, where there is a bolus or continuous feed media supplementation to replenish the nutrients which are consumed. This cell culture technique has the potential to obtain high cell densities in the order of greater than $10 \times 10^6$ to $40 \times 10^6$ cells/ml, depending on the media formulation, cell line, and other cell growth conditions. A biphasic culture condition can be created and sustained by a variety of feed strategies and media formulations.

Alternatively a perfusion culture can be used. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of cell retention techniques including centrifugation, sedimentation, or filtration (see for example Voisard et al., 2003).

When using the methods and/or cell culture techniques of the instant invention, the protein with a modulated mannosylation profile are generally directly secreted into the culture medium. Once said protein is secreted into the medium, supernatants from such expression systems can be first concentrated using a commercially available protein concentration filter.

As used herein, "cell density" refers to the number of cells in a given volume of culture medium. "Viable cell density" refers to the number of live cells in a given volume of culture medium, as determined by standard viability assays. The cell density will be considered as maintained if it is in the range of about −10% to +10% compared to the control culture condition. It will be considered as increased if it is above +10% compared to the control culture condition and will be considered as decreased if it is below −10% compared to the control culture condition.

The term "viability", or "cell viability" refers to the ratio between the total number of viable cells and the total number of cells in culture. Viability is usually acceptable as long as it is at not less than 60% compared to the start of the culture (however, the acceptable threshold can be determined case by case). Viability is often used to determine time for harvest. For instance, in fed-batch culture, harvest can be performed once viability reaches at least 60% or after 14 days in culture. The viability will be considered as maintained if it is in the range of about −10% to +10% compared to the control culture condition. It will be considered as increased if it is above +10% compared to the control culture condition and will be considered as decreased if it is below −10% compared to the control culture condition.

The term "titre" refers to the amount or concentration of a substance, here the protein of interest, in solution. It is an indication of the number of times the solution can be diluted and still contain detectable amounts of the molecule of interest. It is calculated routinely for instance by diluting serially (1:2, 1:4, 1:8, 1:16, etc.) the sample containing the protein of interest and then using appropriate detection method (colorimetric, chromatographic etc.), each dilution is assayed for the presence of detectable levels of the protein of interest. Titre can also be measured by means such as by PA-HPLC (as used in the example section), FortéBio Octet® or with Biacore C®. The titre will be considered as maintained if it is in the range of about −10% to +10% compared to the control culture condition. It will be considered as increased if it is above +10% compared to the control culture condition and will be considered as decreased if it is below −10% compared to the control culture condition.

The term "modulated mannosylation profile" or "modulated mannosylation level" means a mannosylation profile/level of a recombinant protein (for example a therapeutic protein or antibody) that is modulated as compared to the mannosylation profile/level of that same protein produced by culturing a recombinant cell expressing that recombinant protein in cell culture media which is not supplemented with a polyether ionophore such as maduramycin, narasin or salinomycin. The modulated mannosylation profile/level is for instance an increase of high mannose species in said protein. In an embodiment, the modulated mannosylation profile/level may include overall increase in the level of mannosylation of the protein, such as an increase of high mannose species in said protein. The mannosylation level (total level or for each species) will be considered as maintained if it is in the range of about −10% to +10% compared to the control culture condition. It will be considered as increased if it is above +10% compared to the control culture condition and will be considered as decreased if it is below −10% compared to the control culture condition.

The term "protein" as used herein includes peptides and polypeptides and refers to compound comprising two or more amino acid residues. A protein according to the present invention includes but is not limited to a cytokine, a growth factor, a hormone, a fusion protein (such as an Fc-fusion protein), an antibody or a fragment thereof. A therapeutic protein refers to a protein that can be used or that is used in therapy.

The term "recombinant protein" means a protein produced by recombinant technics. Recombinant technics are well within the knowledge of the skilled person (see for instance Sambrook et al., 1989, and updates).

The term "antibody", and its plural form "antibodies", includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). Genetically engineered intact antibodies or fragments, such as SEEDbodies, chimeric antibodies, scFv and Fab fragments, as well as synthetic antigen-binding peptides and polypeptides, are also included.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor" (humanization by grafting non-human CDRs onto human framework and constant regions, or by incorporating the entire non-human variable domains onto human constant regions (chimerization)). Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and a few residues in the heavy chain constant region if modulation of the effector functions is needed, are substantially identical to corresponding parts of natural human immunoglobulin sequences. Through humanizing antibodies, biological half-life may be increased, and the potential for adverse immune reactions upon administration to humans is reduced.

The term "fully human" immunoglobulin refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibodies" means antibodies produced by recombinant technics. Because of the relevance of recombinant DNA techniques in the generation of antibodies, one needs not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

The term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv", "single-chain antibodies," "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

Examples of known antibodies which can be produced according to the present invention include, but are not limited to, adalimumab, alemtuzumab, atezolizumab, avelumab, belimumab, bevacizumab, canakinumab, certolizumab pegol, cetuximab, denosumab, eculizumab, golimumab, infliximab, natalizumab, nivolumab, ofatumumab, omalizumab, pembrolizumab, pertuzumab, pidilizumab ranibizumab, rituximab, siltuximab, tocilizumab, trastuzumab, ustekinumab or vedolizomab. Units, prefixes and symbols are used according to the standards (International System of Units (SI)). Most naturally occurring proteins comprise carbohydrate or saccharide moieties attached to the peptide via specific linkages to a select number of amino acids along the length of the primary peptide chain. Thus, many naturally occurring peptides are termed "glycopeptides" or "glycoproteins" or are referred to as "glycosylated" proteins or peptides. The predominant sugars found on glycoproteins are fucose, galactose, glucose, mannose, N-acetylgalactosamine ("GalNAc"), N-acetylglucosamine ("GlcNAc"), xylose and sialic acid. The oligosaccharide structure attached to the peptide chain is known as a "glycan" molecule. The nature of glycans impact the tridimensional structure and the stability of the proteins on which they are attached. The glycan structures found in naturally occurring glycopeptides are divided into two main classes: "N-linked glycans" or N-linked oligosaccharides" (main form in eukaryotic cells) and "O-linked glycans" or O-linked oligosaccharides". Peptides expressed in eukaryotic cells typically comprise N-glycans. The processing of the sugar groups for N-linked glycoproteins occurs in the lumen of the endoplasmic reticulum (ER) and continues in the Golgi apparatus. These N-linked glycosylations occur on asparagine residue in the peptide primary structure, on sites containing the amino acid sequence asparagine-X-serine/threonine (X is any amino acid residue except proline and aspartic acid). Main glycans that can be found on the antibody or fragments thereof secreted by CHO cells are presented in Table 1:

TABLE 1 main glycan structures

| Glycan name | Glycan structure |
| --- | --- |
| G0 | |
| G0F | |
| G1 | |
| G1F | |
| G1F | |
| G2F | |
| G2F sialyated | |

TABLE 1-continued main glycan structures

| Glycan name | Glycan structure |
|---|---|
| Man5 (=M5) | |
| Man6 (=M6) | |
| Man7 (=M7) | |
| Man8 (=M8) | |
| Man9 (=M9) | |

(legend: squares: GlcNAc; black circles: mannose, white circles: galactose; triangles: fucose; diamond: sialic acid)

The term "Glycoform" refers to an isoform of a protein, such as an antibody or a fragment thereof, differing only in the number and/or type of attached glycans. Usually, a composition comprising a glycoprotein comprises a number of different glycoforms of said glycoprotein. Techniques for the determination of glycan primary structure are well known in the art and are described in detail, for example, in Roth et al. (2012) or Song et al. (2014). It is routine to isolate proteins produced by a cell and to determine the structure(s) of their N-glycans. N-glycans differ with respect to the number of branches (also called "antennae") comprising sugars, as well as in the nature of said branch(es), which can include in addition to the man3GlcNac2 core structure for instance N-acetylglucosamine, galactose, N-acetylgalactosamine, N-acetylneuraminic acid, fucose and/or sialic acid. For a review of standard glycobiology nomenclature see Varki et al., 1999. The N-glycans structures on proteins comprise at least three residues of mannose. These structures can be further mannosylated. The mannosylated glycans such as Man5, Man6, Man7, Man8 or Man9 are called high-mannose glycans (or high-mannose species) (see above Table 1). The term "subject" is intended to include (but not limited to) mammals such as humans, dogs, cows, horses, sheep, goats, cats, mice, rabbits, or rats. More preferably, the subject is a human. The present invention provides methods and compositions for modulating the mannosylation profile of a recombinant protein such as therapeutic protein or antibody. The present invention is based on the optimization of cell culture conditions for protein manufacturing, such as production of antibodies or antigen-binding fragments, resulting in the production of a recombinant protein with modulated mannosylation profiles, preferably with increased mannosylation level (such as increased level of the high-mannose species). Maduramycin (or maduramicin) is a polyether ionophore first isolated from the actinomycete Actinomadura *rubra*. It forms complexes with monovalent cations, with a higher affinity for K+ than Na+. Its Cas Number is 79356-08-4. Its chemical formula is:

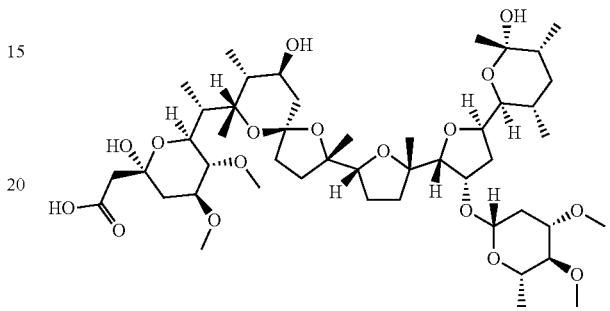

Salinomycin is another polyether ionophore. Its Cas Number is 53003-10-40. Its chemical formula is:

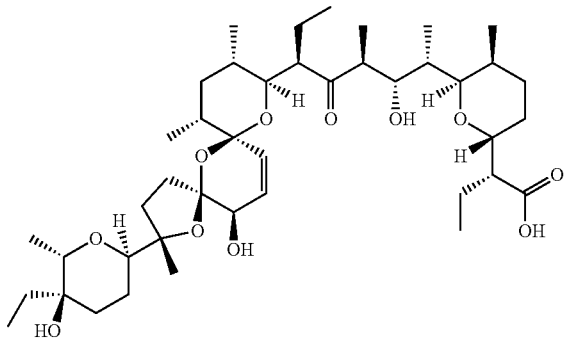 [SMILES: CC[C@@H](C(=O)[C@@H](C)[C@@H](O)[C@H](C)[C@@H]1O[C@@H]([C@@H](CC)C(=O)O)CC[C@@H]1C)[C@H]1O[C@]2(C=C[C@@H](O)[C@]3(CC[C@@](C)([C@H]4CC[C@](O)(CC)[C@H](C)O4)O3)O2)[C@H](C)C[C@@H]1C]

Narasin is another example of polyether ionophore. It is a derivative of salinomycin with an additional methyl group. Its Cas Number is 55134-13-9. Its chemical formula is:

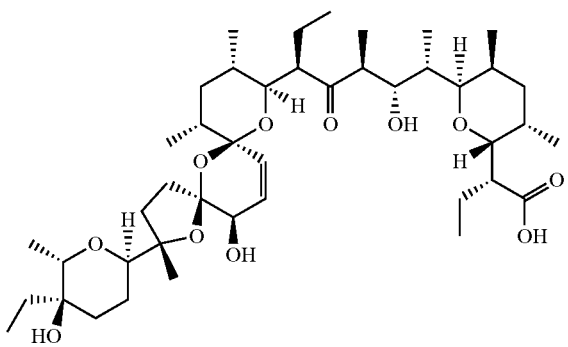 [SMILES: CC[C@@H](C(=O)O)[C@@H]1O[C@@H]([C@@H](C)[C@H](O)[C@H](C)C(=O)[C@H](CC)[C@H]2O[C@]3(C=C[C@@H](O)[C@]4(CC[C@@](C)([C@H]5CC[C@](O)(CC)[C@H](C)O5)O4)O3)[C@H](C)C[C@@H]2C)[C@@H](C)C[C@@H]1C]

Lasalocid is a polyether ionophore produced by Streptomyces lasaliensis. Its Cas Number is 25999-31-9. Its chemical formula is:

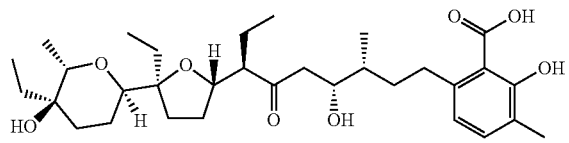 [SMILES: CC[C@@H](C(=O)C[C@@H](O)[C@H](C)CCc1ccc(C)c(O)c1C(=O)O)[C@@H]1CC[C@@](CC)([C@H]2CC[C@](O)(CC)[C@H](C)O2)O1]

It was observed that under cell culture conditions supplemented with a polyether ionophore (or polyether ionophore compound), such as maduramycin, narasin, salinomycin, the mannosylation glycoform content of the recombinant protein increased (more especially the content of high-mannose species). Thus during the cell culture production run, when it is desirable to modulate mannosylation profile of a recombinant protein, such as the high-mannose species level in the recombinant protein being produced, the cell culture can be supplemented with a polyether ionophore, such as maduramycin, narasin, salinomycin, or can be fed with a feed medium containing a polyether ionophore, such as maduramycin, narasin, salinomycin. Alternatively, the cell culture medium can already comprise said polyether ionophore. It was also observed that under specific cell culture conditions supplemented with a polyether ionophore, cell growth, viability and titre were not deeply impacted compared to cell grown without polyether ionophore; it is noted that such cells grown without polyether ionophore correspond to the control according to the present invention.

In one aspect the invention provides a method of producing a recombinant protein with a modulated mannosylation profile said method comprising culturing a recombinant cell expressing said protein in cell culture medium comprising or supplemented with a polyether ionophore.

Alternatively, the present invention describes a method of producing a recombinant protein with a modulated mannosylation profile said method comprising culturing a host cell expressing said protein in cell culture medium complemented with at least one feed comprising a polyether ionophore.

In an embodiment, here is provided the use of a polyether ionophore in a cell culture medium or in a feed medium for modulating the glycosylation profile (e.g. modulating the mannosylation profile) of recombinant proteins produced in mammalian cells.

In a further aspect the invention provides a composition comprising a cell culture medium or a feed medium comprising a polyether ionophore.

In a further aspect the invention provides use of a polyether ionophore, such as maduramycin, narasin or salinomycin for modulating the mannosylation profile of recombinant proteins produced in mammalian cells.

The preferred polyether ionophore compound, in the context of the present invention as a whole, is selected from the group consisting of maduramycin, narasin or salinomycin.

Preferably, in the context of the invention as a whole, the modulated mannosylation profile of the protein is an increase in the overall mannosylation level in the recombinant protein, compared to a control (i.e. cells grown without polyether ionophore). More particularly the increase in mannosylation level is mainly due to an increase in Man5 species, as well as Man6 and Man7 forms although to a lesser extent. Preferably, the overall mannosylation level, as well as the individual levels of each one of the high mannose species (such as Man5, Man6, Man7, Mang, Man9), is at least twice as much as the control, such as at least 100% increased, or at least 150% increased or at least 200% increase compared to a control (relative change). As per the definition section, the modulation of the mannosylation level or the increase in mannosylation level is expressed in relation to the mannosylation level of the same protein produced by culturing a recombinant cell expressing said recombinant protein in cell culture media which is not supplemented with a polyether ionophore.

The recombinant protein (or the protein of interest) to be produced, in the context of the present invention as a whole, can be a therapeutic protein, a fusion protein (such as an Fc-Fusion protein), an antibody or antigen binding fragment thereof, such as a human antibody or antigen-binding portion thereof, a humanized antibody or antigen-binding portion thereof, a chimeric antibody or antigen-binding portion thereof. Preferably, it is an antibody or antigen binding fragment thereof.

The methods of the present invention can be used to produce any protein of interest having increased amounts or levels of mannosyl residues. Modulating the mannosyl level of an antibody, for instance, may indeed be needed to reach, or to maintain, a certain CDC and/or ADCC level.

In the context of the invention as a whole, the polyether ionophore compound, such as maduramycin, narasin or salinomycin, is added in a cell culture medium before or after seeding (i. e. inoculation). Preferably, the polyether ionophore compound is added in the cell culture medium in order to reach a concentration after seeding (i.e. after inoculation) of or of about 0.5 to 250 nM, preferably of or of about 1 to 200 nM, even preferably of or of about 2 to 150 nM such as at concentration of or of about 2, 5, 10, 15, 20, 30, 40, 50, 60, 70, 80, 90, 100, 110, 120 nM. For example, by adjusting the concentration of a polyether ionophore compound the mannosylation profile can be modulated. Should the polyether ionophore compound be added to a cell culture medium before seeding, the dilution factor linked to the inoculation itself has to be taken into account. By knowing the culture medium volume at the time the supplementation is made and the volume of the cell culture after seeding (or the volume of inoculum added), it is easy to calculate the dilution factor. Said dilution factor is typically ranged from 10 to 15%. However, it can be up to 30% in case of high seeding. For instance, should one targets the equivalent of about 10 nM after seeding and the dilution factor being of 10%, the polyether ionophore will have to be added at a final concentration (before inoculation) of respectively about 11 nM. This final concentration has to be understood as the final concentration for the given supplement/feed once in the culture medium. Indeed, and as an example, the skilled person will understand that should the polyether ionophore compound be added during culture in 2 feeds, the total final concentration will correspond to the final concentration of the second supplement/feed, added to the remaining final concentration of the first supplement/feed. It is noted that the concentration of the polyether ionophore will have to be adapted cell line per cell line as a function of the toxicity of each compound for the cell line of interest. For instance, should a compound start being toxic (e.g. VCD decreased by a factor 3 at day 3 compared to the control) at around 200 nM, it would be advisable to test it at a concentration about 10 times lower (e.g. 20 nM).

For the purposes of this invention, cell culture medium is a medium suitable for growth of animal cells, such as mammalian cells, in in vitro cell culture. Cell culture media formulations are well known in the art. Cell culture media may be supplemented with additional components such as sugars, vitamins, hormones, and growth factors, depending on the needs of the cells in culture. Preferably, the cell culture media are free of animal components; they can be serum-free and/or protein-free.

In certain embodiments of the present invention, the cell culture medium is supplemented with the polyether ionophore, for example, at the start of culture, and/or in a fed-batch or in a continuous manner. The addition of the polyether ionophore supplement may be based on measured intermediate mannosylation profiles/levels. Said addition during culture can be done via a feed consisting only of polyether ionophore compound or via a feed comprising the supplement of polyether ionophore compound among other components.

In an embodiment of the present invention, the host cell is preferably a mammalian host cell (herein also refer to as a mammalian cell) including, but not limited to, HeLa, Cos, 3T3, myeloma cell lines (for instance NS0, SP2/0), and Chinese hamster ovary (CHO) cells. In a preferred embodiment, the host cell is Chinese Hamster Ovary (CHO) cells, such as CHO-S cell and CHO-k1 cell.

In the context of the invention as a whole, the recombinant cell, preferably mammalian cell, is grown in a culture system such as a bioreactor. The bioreactor is inoculated with viable cells in a culture medium comprising or supplemented with a polyether ionophore compound. Preferably the culture medium is serum-free and/or protein-free. Once inoculated into the production bioreactor the recombinant cells undergo an exponential growth phase. The growth phase can be maintained using a fed-batch process with bolus (or continuous) feeds of a feed medium optionally supplemented with said polyether ionophore or of a feed consisting of polyether ionophore. Preferably the feed medium is serum-free and/or protein-free. These supplemental feeds typically begin shortly after the cells are inoculated into the bioreactor, at a time when it is anticipated or determined that the cell culture needs feeding. For example, supplemental feeds can begin on or about day 3, 4 or 5 after the start of the culture or a day or two earlier or later. The culture may receive one, two, three, or more bolus (or continuous) feeds during the growth and production phases. Any one of these feeds can optionally be supplemented with the polyether ionophore. The supplementation or the feed with the polyether ionophore can be done at the start of the culture, in fed-batch, and/or in continuous manner. Alternatively, the supplementation with the polyether ionophore compound can be performed only after the start of the culture: in such a case the polyether ionophore will not be added in the culture medium at the start of the culture (e.g. at the time of inoculation). When the polyether ionophore is added as a feed, it can be supplemented separately (as a single component feed) or together with the usual supplemental feed (as part of another type of feed). Said feed of polyether ionophore can begin on or about day 3, 4 or 5 after the start of the culture or a day or two earlier or later (such as day 1, day 2, day 6 or day 7). The culture may receive two, three, or more feeds during the growth and production phases. For instance, but not to be seen as limiting examples, 1) a first feed of polyether ionophore can be added on day 3, followed by additional polyether ionophore feeds on days 5, 7 and 10 or 2) a first feed of polyether ionophore can be added on day 5, followed by additional polyether ionophore feeds on days 7 and 10. Should the culture duration be longer than 12-14 days, such as 21-24 days, number and timing of feeds can be adapted (e.g. feeds up to days 15, 16 or 17 for instance). The supplementation/feeding strategy depends on the target mannosylation profile and on the culture duration, and can be adapted case by case based on the present disclosure.

The methods, compositions and uses according to the present invention may be used to improve the production of recombinant proteins in multistep culture processes. In a multiple stage process, cells are cultured in two or more distinct phases. For example cells are cultured first in one or more growth phases, under conditions improving cell proliferation and viability, then transferred to production phase (s), under conditions improving protein production. In a multistep culture process, some conditions may change from one step (or one phase) to the other: media composition, shift of pH, shift of temperature, etc. The growth phase can be performed at a temperature higher than in production phase. For example, the growth phase can be performed at a first temperature from about 35° C. to about 38° C., and then the temperature is shifted for the production phase to a second temperature from about 29° C. to about 37° C. The cell cultures can be maintained in production phase for days or even weeks before harvest.

The cell lines (also referred to as "recombinant cells") used in the invention are genetically engineered to express a protein of commercial or scientific interest. Methods and vectors for genetically engineering of cells and/or cell lines to express a polypeptide of interest are well known to those of skill in the art; for example, various techniques are illustrated in Ausubel et al. (1988, and updates) or Sambrook et al. (1989, and updates). The methods of the invention can be used to culture cells that express recombinant proteins of interest. The recombinant proteins are usually secreted into the culture medium from which they can be recovered. The recovered proteins can then be purified, or partially purified using known processes and products available from commercial vendors. The purified proteins can then be formulated as pharmaceutical compositions. Suitable formulations for pharmaceutical compositions include those described in Remington's Pharmaceutical Sciences, 1995.

In a further aspect, the invention provides a composition comprising a recombinant protein with a modulated mannosylation profile produced by the methods of the invention.

The compositions of the invention comprising a recombinant protein with a modulated mannosylation profile, for example an Fc-fusion protein, an antibody or antigen-binding fragment thereof, with an increased mannosylation level or amount, may be used to treat any disorder in a subject for which the therapeutic protein (such as an antibody or an antigen binding fragment thereof) comprised in the composition is appropriate for.

In a further aspect, the invention provides a pharmaceutical composition comprising the recombinant protein with a modulated mannosylation profile produced by the methods of the invention and a pharmaceutically acceptable carrier.

In certain embodiments, the pharmaceutical compositions of the invention comprising a recombinant protein with a modulated mannosylation profile may be formulated with a pharmaceutically acceptable carrier as pharmaceutical (therapeutic) compositions, and may be administered by a variety of methods known in the art (see for instance Remington's Pharmaceutical Sciences, 1995). Such pharmaceutical compositions may comprise any one of salts, buffering agents, surfactants, solubilizers, polyols, amino acids, preservatives, compatible carriers, optionally other therapeutic agents, and combinations thereof. The pharmaceutical compositions of the invention comprising a recombinant protein with a modulated mannosylation profile, are present in a form known in the art and acceptable for therapeutic uses, such as liquid formulation, or lyophilized formulation. Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features.

The foregoing description will be more fully understood with reference to the following examples. Such examples, are, however, exemplary of methods of practising the present invention and are not intended to limit the scope of the invention.

EXAMPLES

Material and Methods
I. Cells, Cell Expansion and Cell Growth

"mAb1" is a humanized monoclonal antibody directed against a receptor found on the cell membrane. Its isoelectric point (pI) is about 8.5-9.5. mAb1 was produced in CHO-S cells.

"mAb2" is an IgG1 fusion protein (i.e. an Fc-Fusion protein), comprising one part directed against a membrane protein (IgG part, comprising an Fc domain) linked to a second part targeting a soluble protein. Its isoelectric point (pI) is about 6.6-8.0. It was expressed in CHO-S cells.

Cells expressing mAb1 and mAb2 were inoculated at $0.2 \times 10^6$ cells per millilitre (mL).

All assays were performed in fed-batch culture. A serum-free chemically defined culture medium was used. It was used as it is, or it was supplemented with polyether ionophore compounds (maduramycin, narasin, salinomycin and lasalocid were all purchased from Sigma-Aldrich) at the desired concentrations. The culture medium was fed, on a regular basis, with a chemically defined feed medium, as well as with glucose in order to keep said glucose level in the range of >0 to about 8 g/L (feeds were done at days 3, 5, 7, 10 and additional glucose feed at day 12).

For example 1, cultures were performed in SpinTubes® with a working volume of 30 mL. They were incubated at 36.5° C., 5% de CO2, 80% humidity and shaken at 320 rpm. Salinomycin, narasin and maduramycin were tested at 100, 250, 500 and 1000 nM.

For examples 2 and 3, cultures were performed in Ambr®15 with a working volume of 14 mL (36.5° C., Dissolved Oxygen 40%, 0.1 ml/min N2, pH range: 6.75-7.15, 800 rpm). A temperature shift was performed at day 6 for the cells expressing mAb1. Further conditions are mentioned in Table 2.

Each of the fed-batch culture lasted 14 days.

II. Analytical Methods

Viable cell density and viability were measured with the ViCell® (Beckmann Coulter). Antibody titers were measured with PA-HPLC.

Glycosylation profiles were established either by Ultra Performance Liquid Chromatography-2-amino-benzamide labelling technique (2AB-UPLC; mAb1) or by mass spectroscopy (MS; mAB2). Groups of glycans were defined in Table 1.

Example 1—Toxicity of the Polyether Ionophores

The cells were cultivated and the results analysed as disclosed in the material and method section. It is noted that the controls (or control conditions) according to the present invention correspond to cells grown without any polyether ionophores.

Viable cell density as a function of elapsed time are shown on FIG. 1 (FIG. 1A for salinomycin; FIG. 1B for narasin and FIG. 1C for maduramycin). At all concentrations tested (i.e. as low as 100 nM) both salinomycin and narasin were very toxic on the cells, decreasing by a factor 3 the VCD. Maduramycin had a comparable toxicity at 250 nM. Maduramycin at 100 nM shows a less severe effect on VCD.

These experimentations allowed to set up the concentrations of each compound for the next experiments.

Example 2—Impact of Polyether Ionophores on mAb1 Antibody

The cells were cultivated and the results analysed as disclosed in the material and method section.

Figure 2:
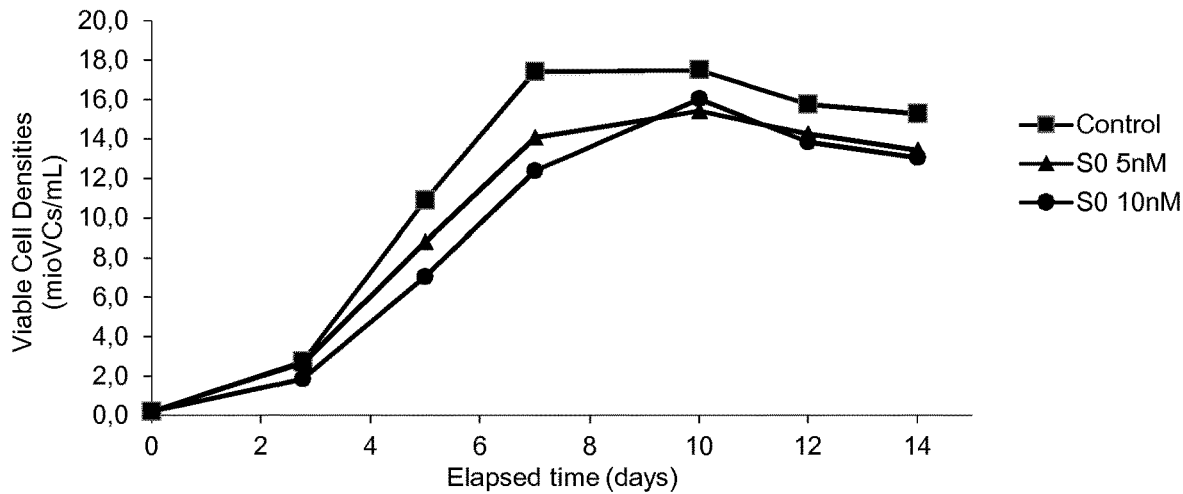
FIG. 2 shows density of viable cells (FIG. 2A; ViCell®) and viability (FIG. 2B; ViCell®) in relation to time as well as titre (FIG. 2C; PA-HPLC) up to day 14 for mAb1 cells cultured at different salinomycin concentrations in minibioreactor Ambr, added at the start of the culture. Results are presented as mean±standard deviation.
Figure 2:
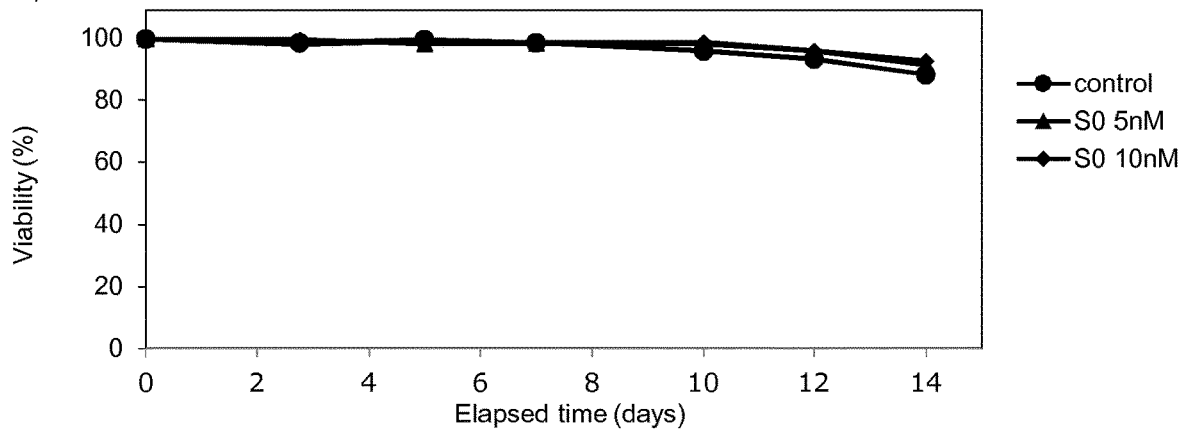
Figure 2:
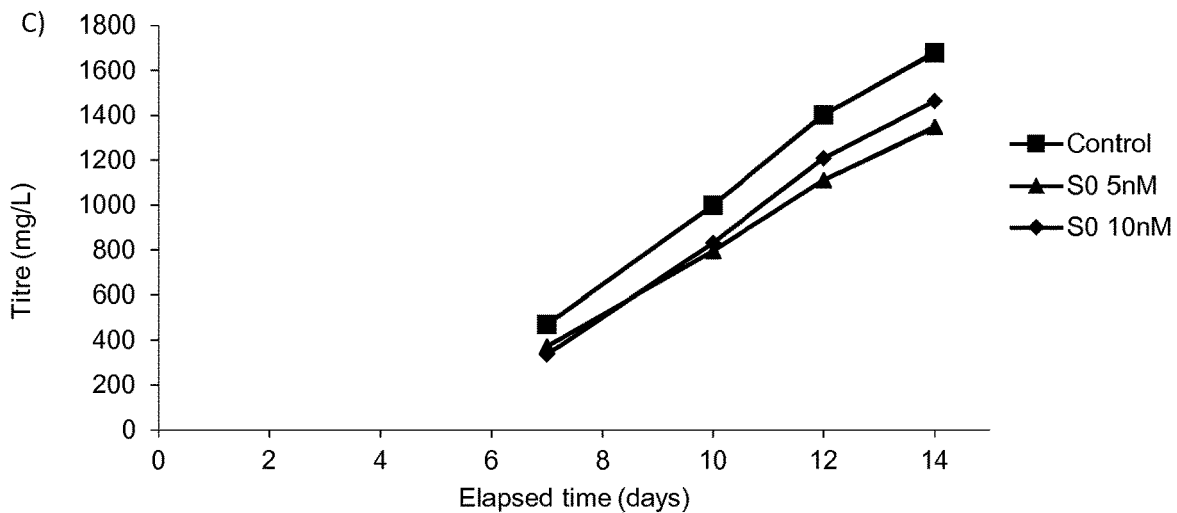
Figure 3:
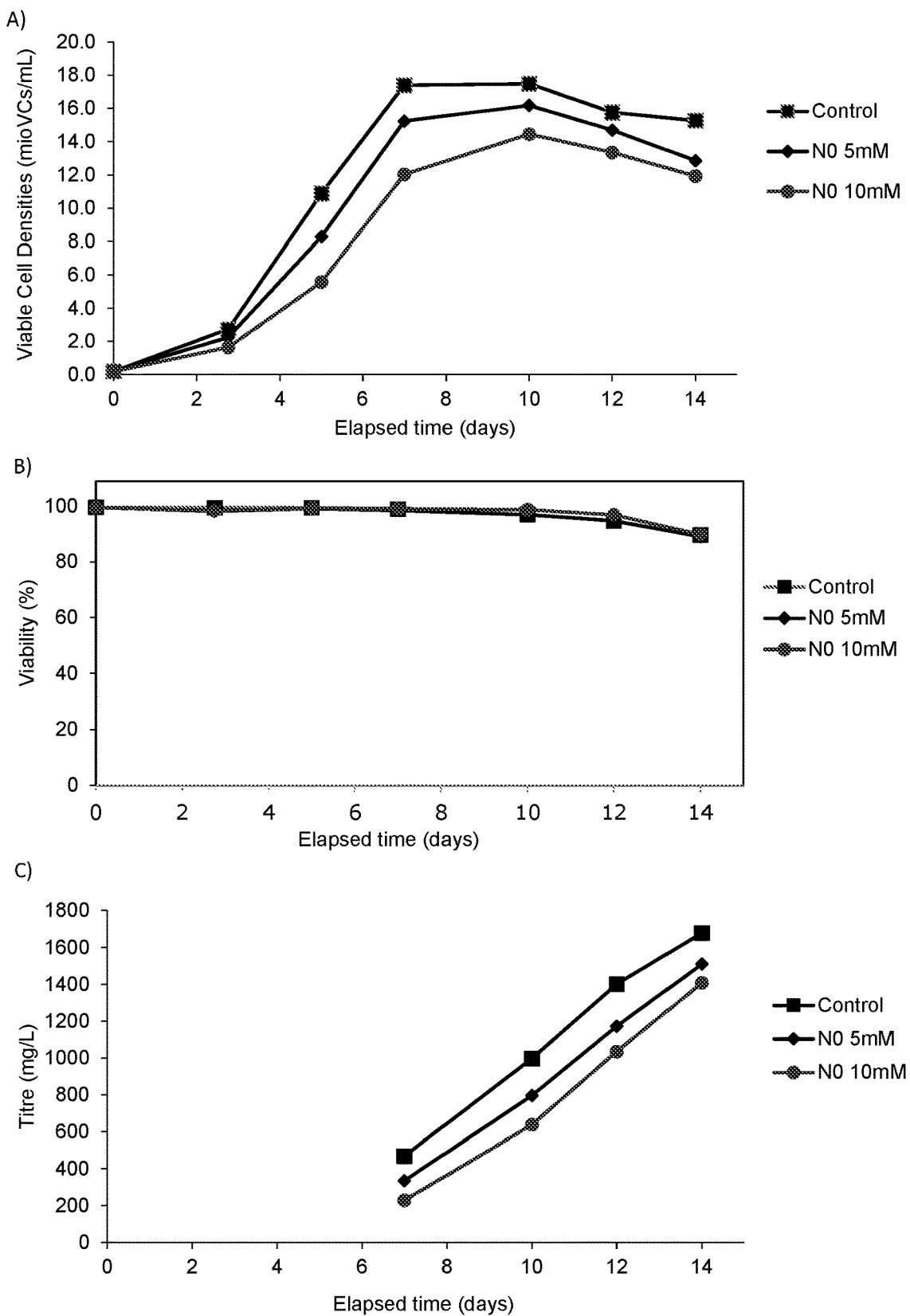
FIG. 3 shows density of viable cells (FIG. 3A; ViCell®) and viability (FIG. 3B; ViCell®) in relation to time as well as titre (FIG. 3C; PA-HPLC) up to day 14 for mAb1 cells cultured at different narasin concentrations in minibioreactor Ambr, added at the start of the culture. Results are presented as mean±standard deviation.
Figure 4:
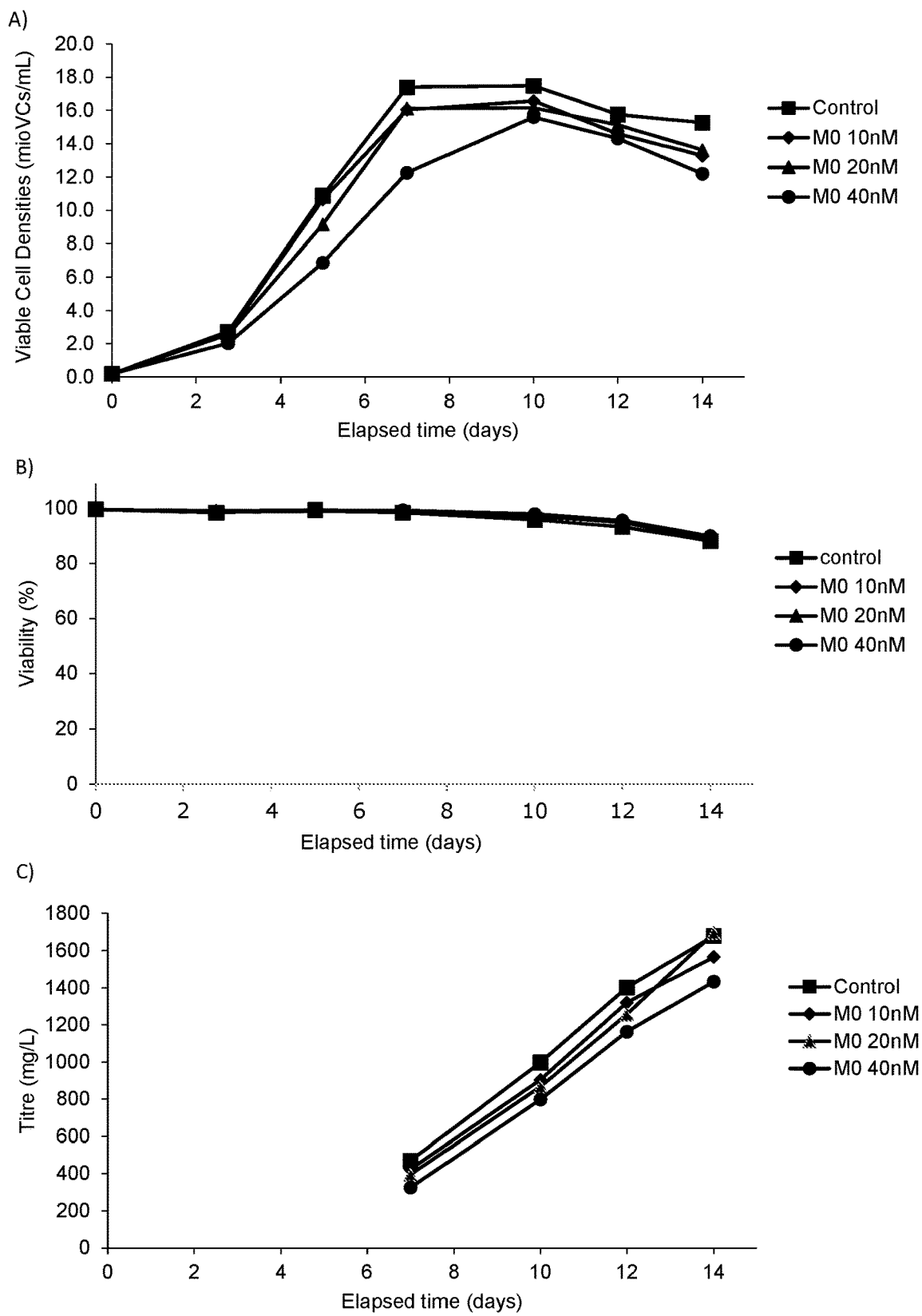
FIG. 4 shows density of viable cells (FIG. 4A; ViCell®) and viability (FIG. 4B; ViCell®) in relation to time as well as titre (FIG. 4C; PA-HPLC) up to day 14 for mAb1 cells cultured at different maduramycin concentrations in minibioreactor Ambr, added at the start of the culture. Results are presented as mean±standard deviation.
Figure 5:
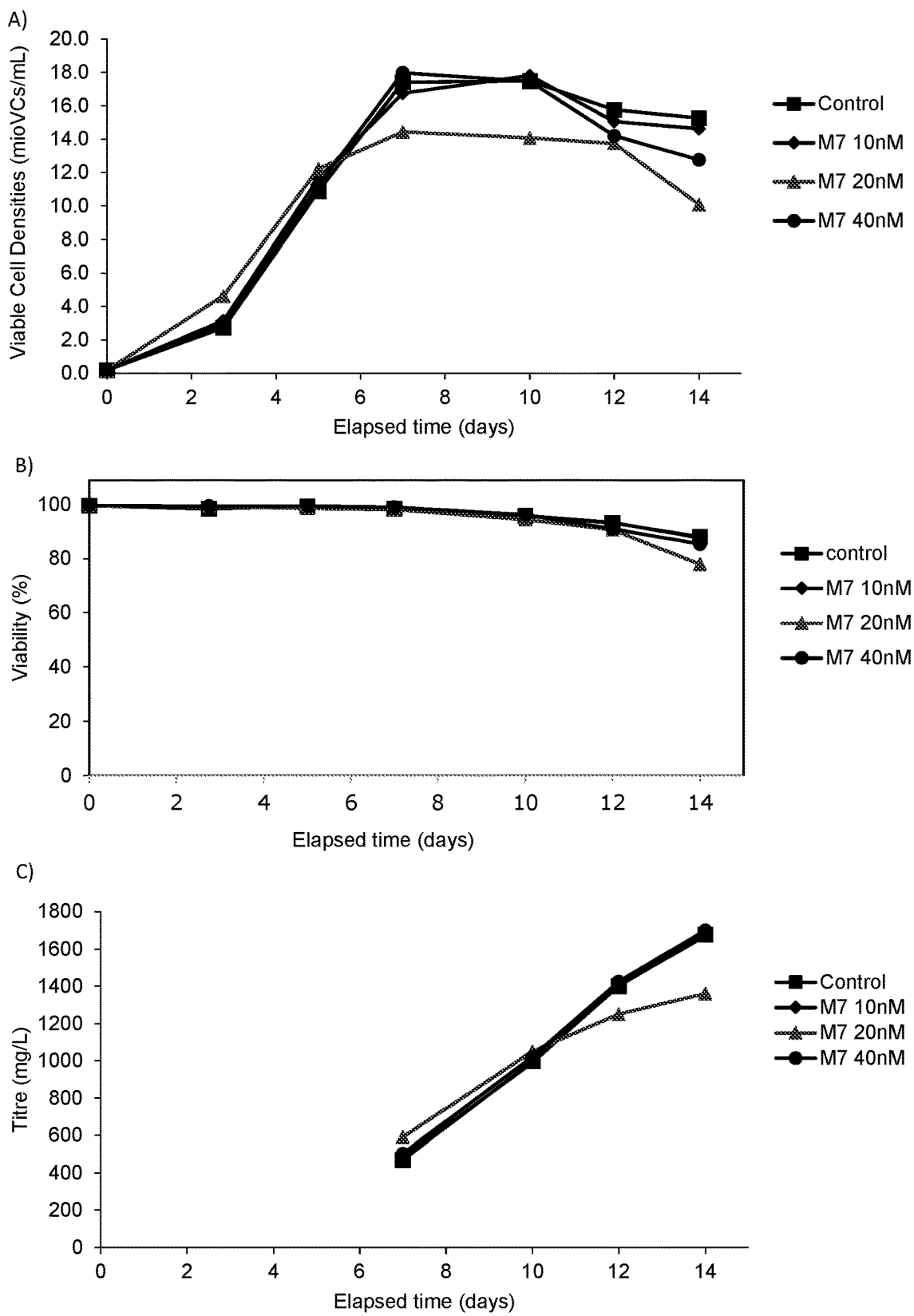
FIG. 5 shows density of viable cells (FIG. 5A; ViCell®) and viability (FIG. 5B; ViCell®) in relation to time as well as titre (FIG. 5C; PA-HPLC) up to day 14 for mAb1 cells cultured at different maduramycin concentrations in minibioreactor Ambr, added at day 7. Results are presented as mean±standard deviation.

Viable Cell Density, Viability and Titre:

Viable cell density, viability as a function of elapsed time, as well as antibody titre at the end of the fed-batch culture are shown on FIGS. 2 to 5 (FIG. 2 for salinomycin; FIG. 3 for narasin, FIG. 4 for maduramycin added at the start of the culture, FIG. 5 for maduramycin added at day 7).

In none of the case viability was impacted: it remained stable, compared to the control, whatever the concentration and whatever the polyether ionophore used.

Addition at the start of the culture: At any one of the concentrations tested, i.e. 5 and 10 nM, both salinomycin and narasin had a slight negative impact on cell growth (respectively −13% and −15%) or protein titre (both at −15%) at the end of culture, compared to the control. Similar results were observed for maduramycin at 40 nM (about 13% decrease of the VCD and about 15% decreased of the titre). To the contrary, maduramycin added at the start of the culture at both 10 and 20 nM demonstrated comparable VCD (not more than −10% at both concentrations) and titre (respectively −6% and +1%) to the control.

Addition at day 7: Maduramycin added at day 7 after the start of the culture at a concentration of 10 nM shown no negative effect on both VCD and titre compared to the control. At 40 nM, maduramycin had a slight negative impact on cell growth (−15%) however, this had no impact on the titre. Interestingly at 20 nM maduramycin had a negative impact on viability. This may be due to an unexpected increase of lactate in this bioreactor. Nevertheless, maduramycin should not be toxic at this concentration in view of the other results with higher concentration.

Figure 6A:
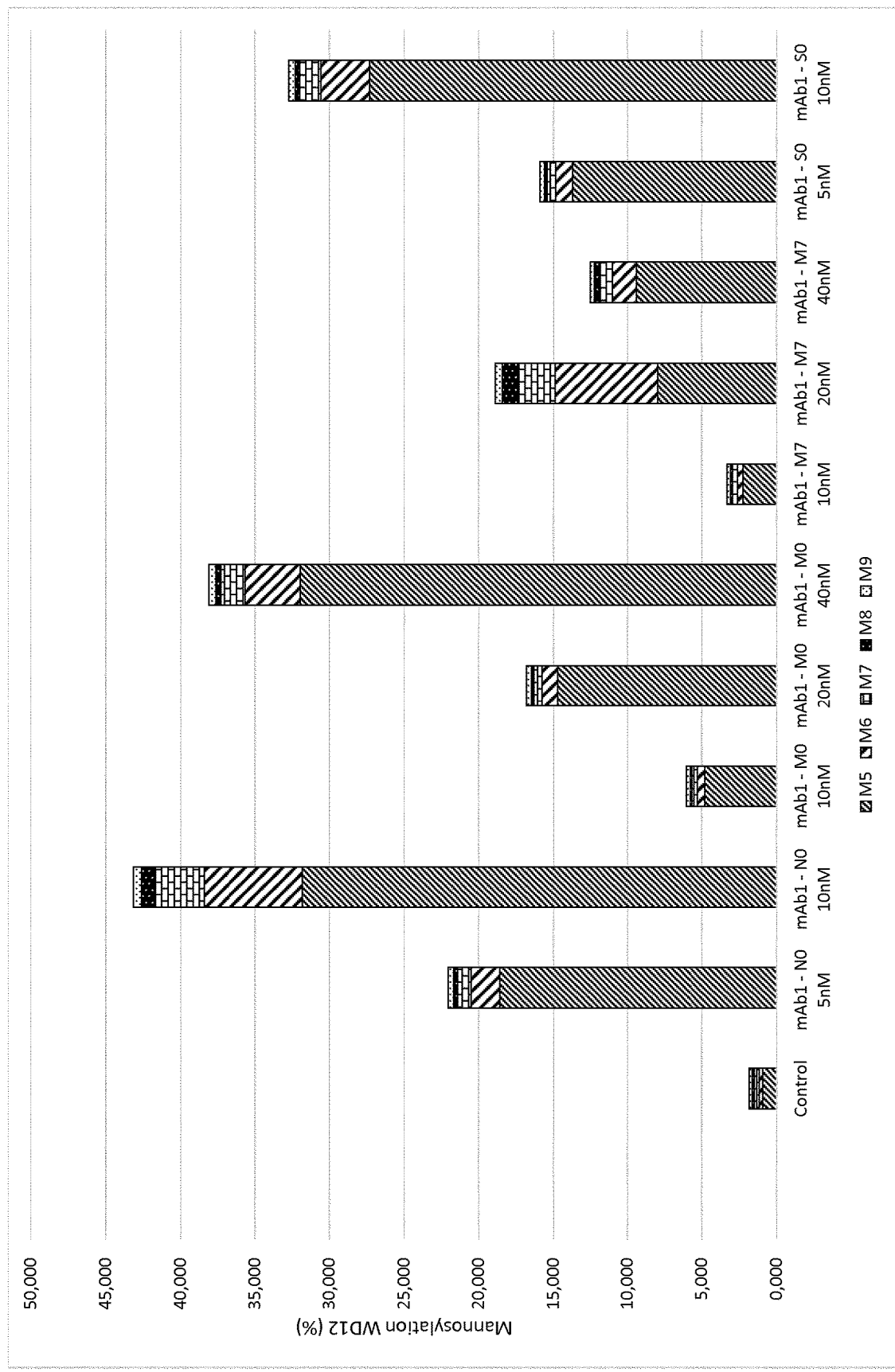
FIG. 6 shows the mannosylation profile at day 12 (FIG. 6A) and day 14 (FIG. 6B) for mAb1 cultured at different polyether ionophores concentrations in minibioreactor Ambr. Results are presented as mean±standard deviation.
Figure 6B:
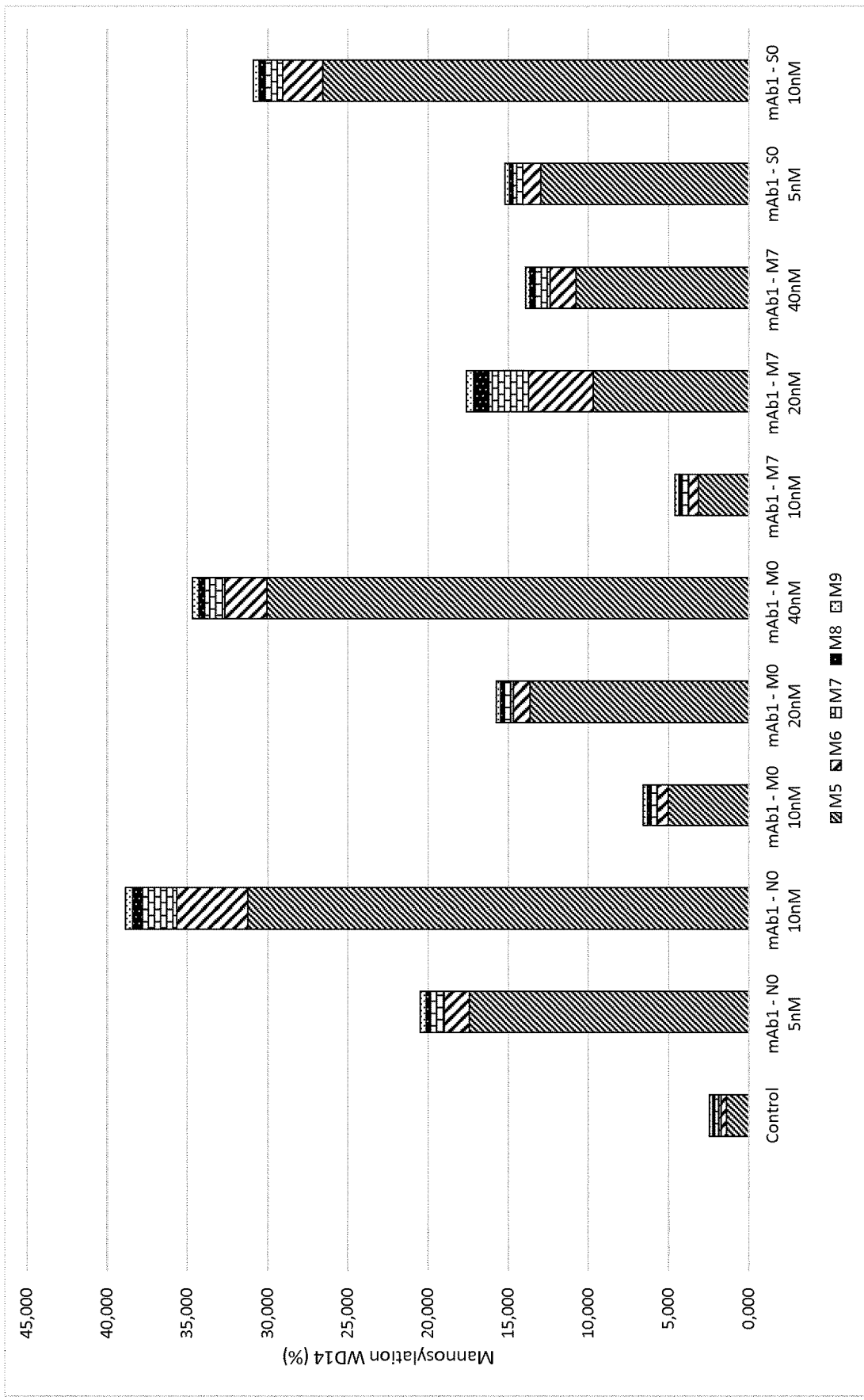

Glycosylation Profiles:

Glycosylation profiles are shown on FIG. 6 (FIG. 6A=at day 12; FIG. 6A=at day 14).

For polyether ionophores added at the start of the culture, the data obtained underlines that:

The polyether ionophores narasin, salinomycin and maduramycin have a strong impact on the mannosylation level of mAb1, compared to the control, especially on ManS species. For example, at day 12, the level of ManS species increased from about 1% (for the control) to up to about 27% with 10 mM of salinomycin or up to about 32% for both 10 mM narasin and 40 nM maduramycin.

The polyether ionophores narasin, salinomycin and maduramycin have an impact on the Man6-Man9 species level of mAb1, compared to the control. For example, at day 12:

The level of Man6 species (M6) increased from about 0.35% (for the control) to up to about 3.7% with 40 mM maduramycin, up to about 3.2% with 10 mM of salinomycin or up to about 6.5% with 10 mM narasin.

The level of Man7 species increased from about 0.35% (for the control) to up to about 1.5% with 40 mM maduramycin or 10 mM salinomycin or up to about 4.5% with 10 mM narasin.

The level of Man8 species increased from about 0.12% (for the control) to up to about 0.3% with 10 mM salinomycin, up to about 1.5% with 40 mM maduramycin or up to about 3.5% with 10 mM narasin.

The level of Man9 species increased from about 0.2% (for the control) to up to about 0.45% with 10 mM salinomycin or up to about 0.5% with 40 mM maduramycin or 10 mM narasin.

The impact on the total mannosylation level varies a lot as a function of the polyether ionophore that is used. For instance, when comparing the effect of salinomycin, narasin and maduramycin at 10 nM, narasin showed the highest mannosylation increase. Indeed using 10 nM narasin, the total mannosylation reached about 43% after 12 days of culture and 38.9% after 14 days of culture. On the contrary, maduramicin had the lowest effect on mannosylation with total mannosylation of 6.1% after 12 days of culture and 6.6% after 14 days of culture. This difference between polyether ionophores could be explained by the different toxicity of these compounds. Indeed toxicity tests showed that at 100 nM maduramicin was the less toxic polyether ionophore compared to the other tested (see example 1).

The impact on the mannosylation level of mAb1, compared to the control, can be modulated as a function of the nature/concentration of the polyether ionophore that is used and the elapsed time in culture (12 or 14 days for example).

For polyether ionophores added as feed during the culture, the data obtained underlined that:

Addition of the compound (such as maduramycin) also impact the mannosylation level.

The main impact is once more mainly on the Man5 species, however a stronger effect has been shown on Man6 and Man7, especially at a concentration of 20 mM of maduramycin.

Conclusion for mAb1:

The present results surprisingly underline that salinomycin, narasin and maduramycin are able to modulate the mannosylation of an antibody, here mAb1, and in particular are able to deeply increase the amount of Man5 species, and to a lesser extend M6 to M9, without deeply impacting afucoslyated glycoforms (increase of only about 1-2%; data non shown). Although not shown, the level of fucosylated glycoforms decreased while Man glycoforms increased (decrease of 3 to 40%). To the contrary, another polyether ionophore, i.e. lasalocid, has no effect on mannosylation. This example shows that the mannosylation can be fine-tune based on the teaching of the present invention by playing with the nature/concentration of the polyether ionophore that is used (salinomycin, narasin or maduramycin), the elapsed time in culture and the timing of addition of the molecule, i.e. at the start of the culture (such as in the cell culture before or just after seeding), or as a feed at a later stage (e.g. day 7 in example 2).

Example 3—Impact of Polyether Ionophores on mAb2 Antibody

The cells were cultivated and the results analysed as disclosed in the material and method section.

Figure 7:
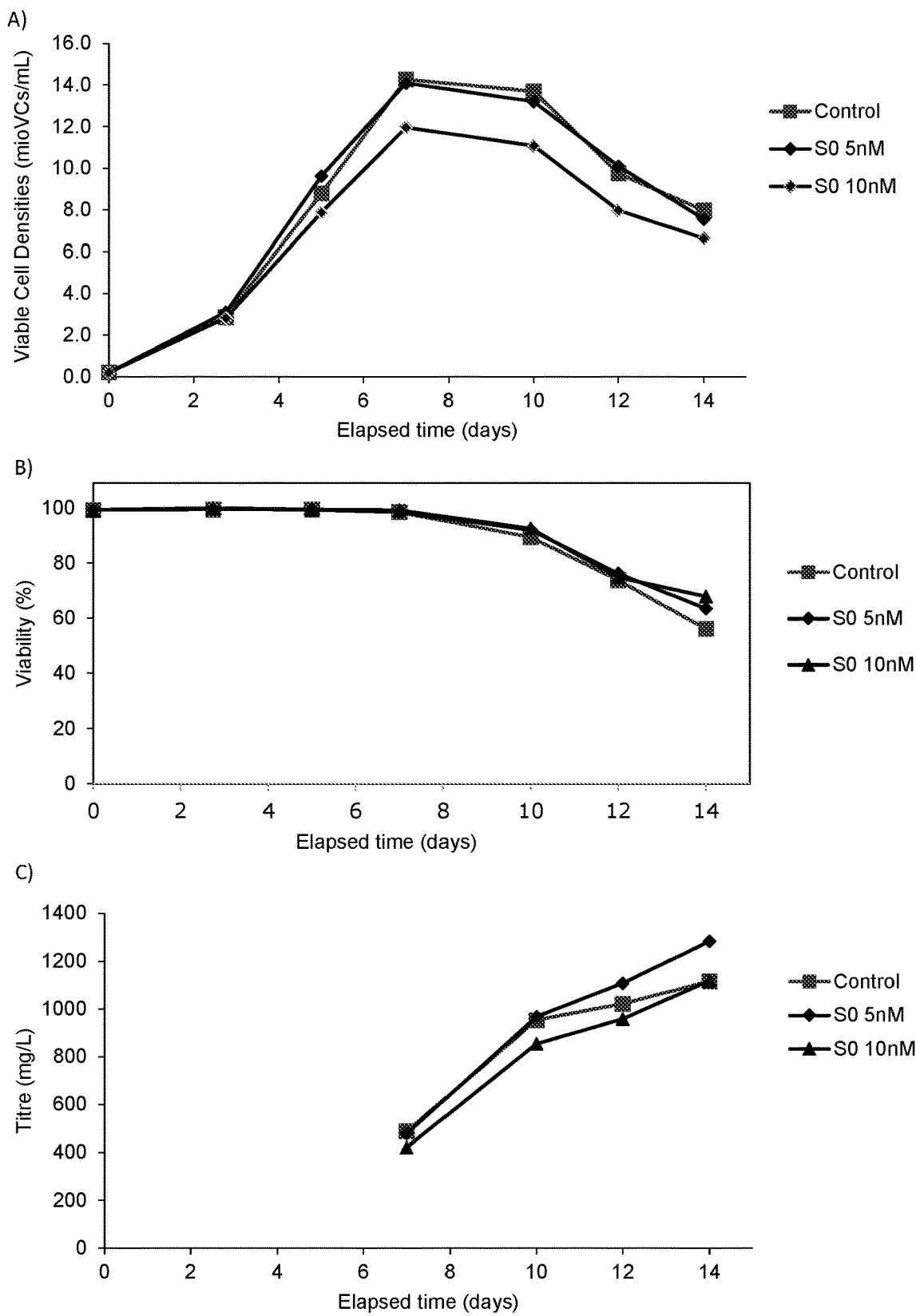
FIG. 7 shows density of viable cells (FIG. 7A; ViCell®) and viability (FIG. 7B; ViCell®) in relation to time as well as titre (FIG. 7C; PA-HPLC) up to day 14 for mAb2 cells cultured at different salinomycin concentrations in minibioreactor Ambr, added at the start of the culture. Results are presented as mean±standard deviation.
Figure 8:
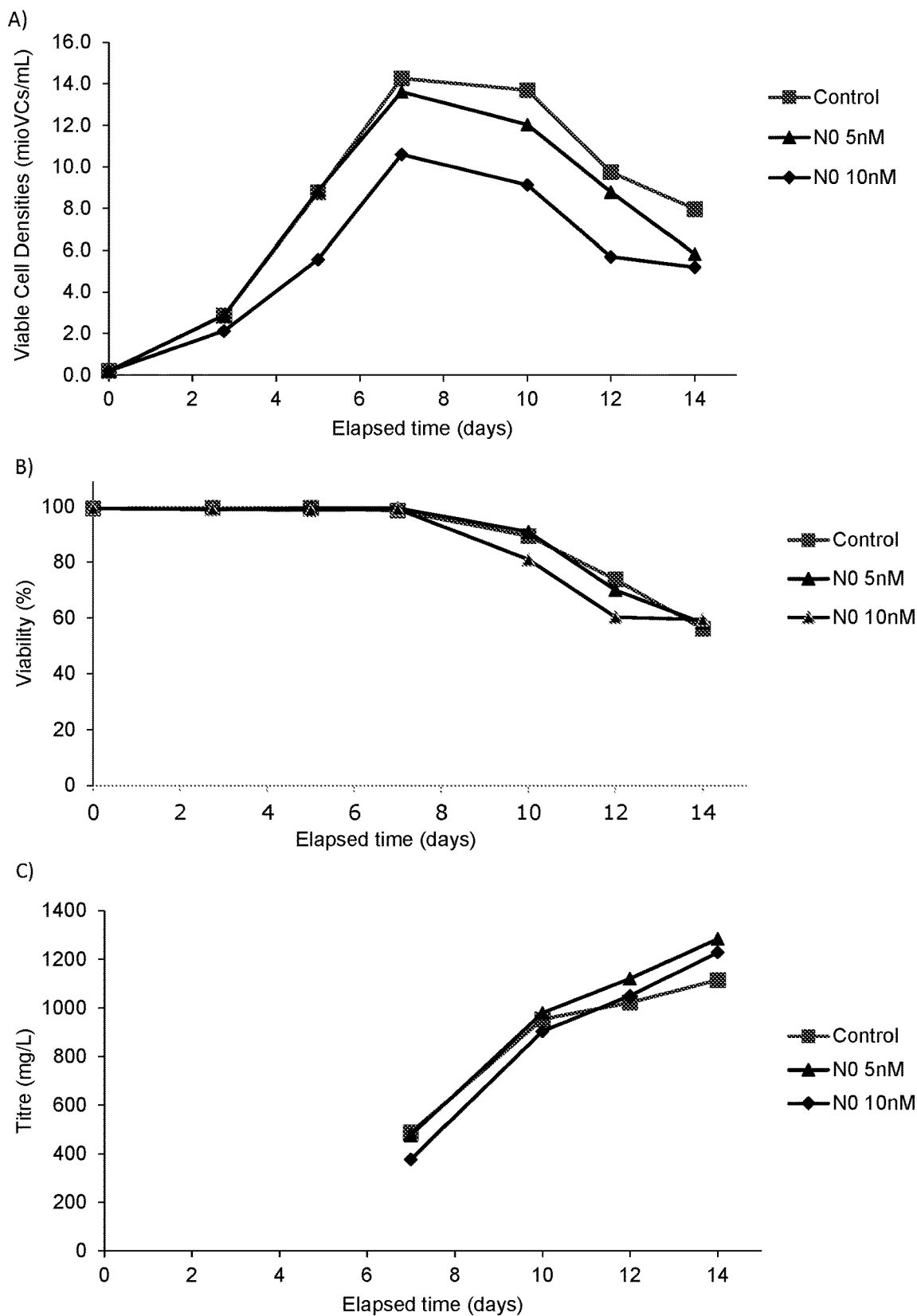
FIG. 8 shows density of viable cells (FIG. 8A; ViCell®) and viability (FIG. 8B; ViCell®) in relation to time as well as titre (FIG. 8C; PA-HPLC) up to day 14 for mAb2 cells cultured at different narasin concentrations in minibioreactor Ambr, added at the start of the culture. Results are presented as mean±standard deviation.
Figure 9:
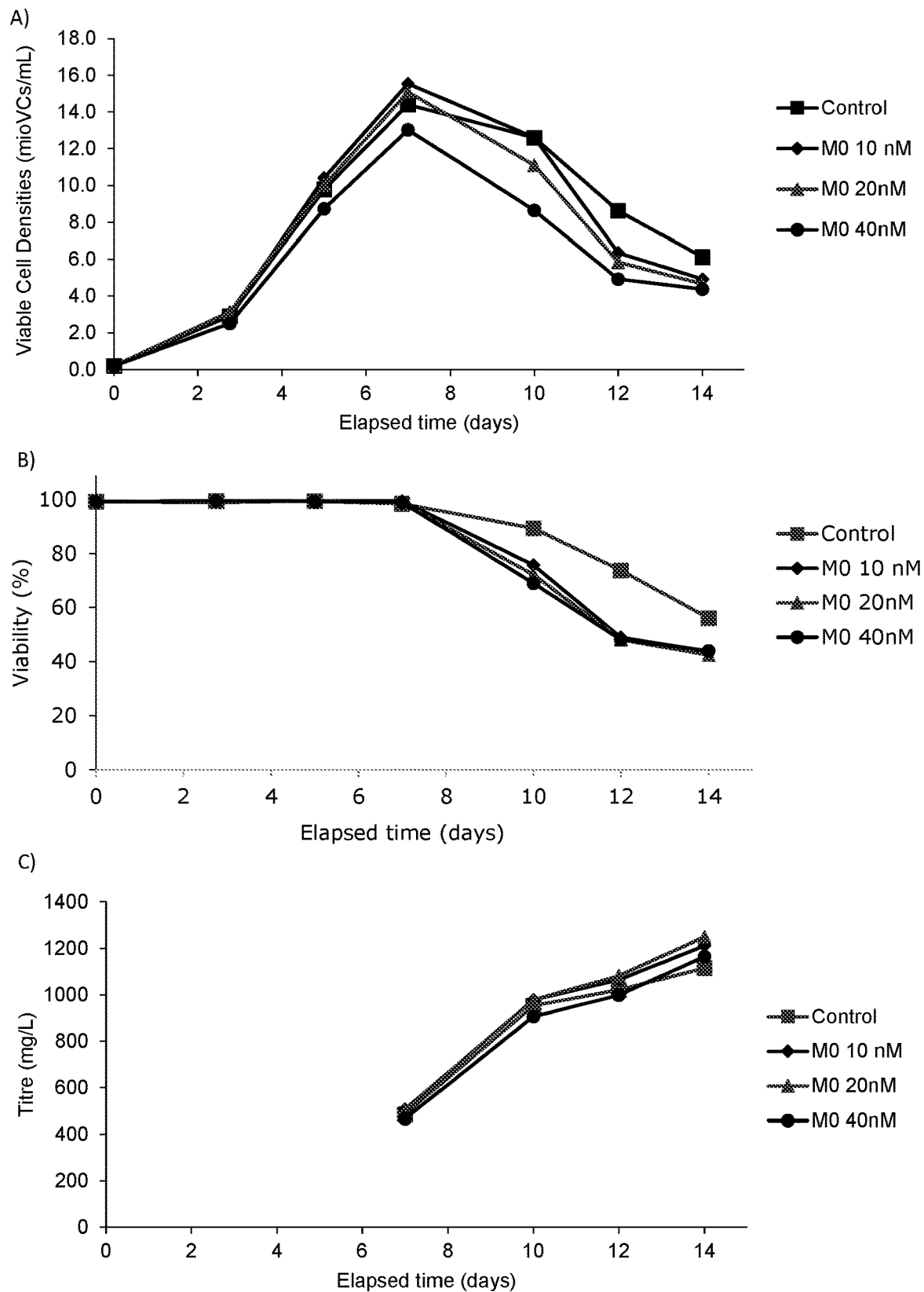
FIG. 9 shows density of viable cells (FIG. 9A; ViCell®) and viability (FIG. 9B; ViCell®) in relation to time as well as titre (FIG. 9C; PA-HPLC) up to day 14 for mAb2 cells cultured at different maduramycin concentrations in minibioreactor Ambr, added at the start of the culture. Results are presented as mean±standard deviation.
Figure 10:
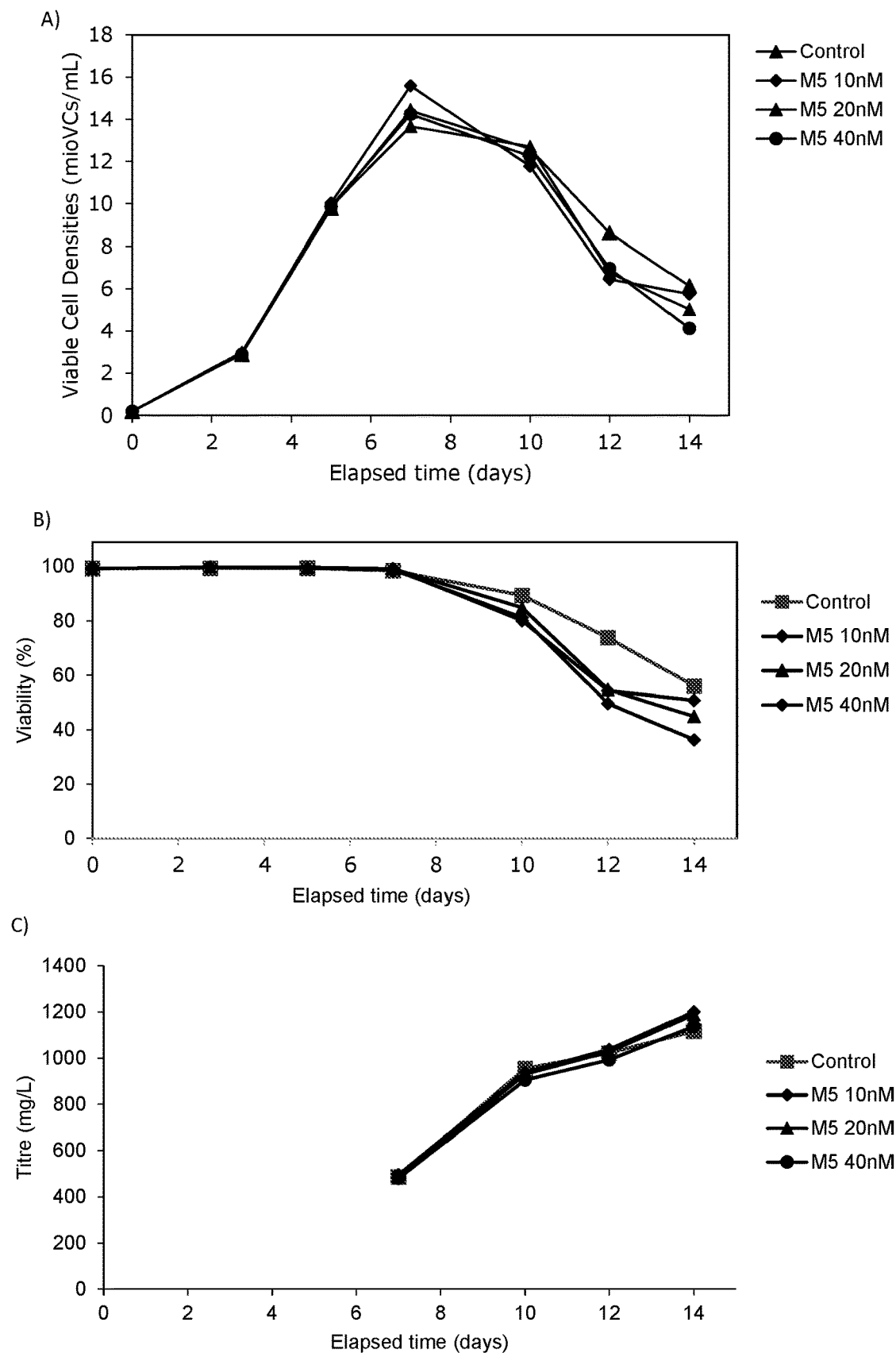
FIG. 10 shows density of viable cells (FIG. 10A; ViCell®) and viability (FIG. 10B; ViCell®) in relation to time as well as titre (FIG. 10C; PA-HPLC) up to day 14 for mAb2 cells cultured at different maduramycin concentrations in minibioreactor Ambr, added at day 5. Results are presented as mean±standard deviation.

Viable Cell Density, Viability and Titre:

Viable cell density, viability as a function of elapsed time, as well as antibody titre at the end of the fed-batch culture are shown on FIGS. 7 to 10 (FIG. 7 for salinomycin; FIG. 8 for narasin, FIG. 9 for maduramycin added at the start of the culture, FIG. 10 for maduramycin added at day 5).

Addition at the start of the culture: At any one of the concentrations tested, i.e. 5 and 10 nM, salinomycin showed comparable cell growth (not more than 10% at 10 nM) or protein titre (up to +10%) to the control at the end of culture. Although having a negative impact on cell growth at both concentration, narasin demonstrated comparable titre at 5 nM (+10%) and a slight positive impact at 10 nM (+15%) to the control. Maduramycin presented a profile similar to narasin on both cell growth and titre (with up to +10 and +12% compared to the control at any concentrations tested).

Addition at day 5: Maduramycin, whatever its concentration, added at day 5 after the start of the culture at a concentration of 10 nM shown no negative effect on the titre compared to the control, although having a negative impact on cell growth starting day 12.

Figure 11A:
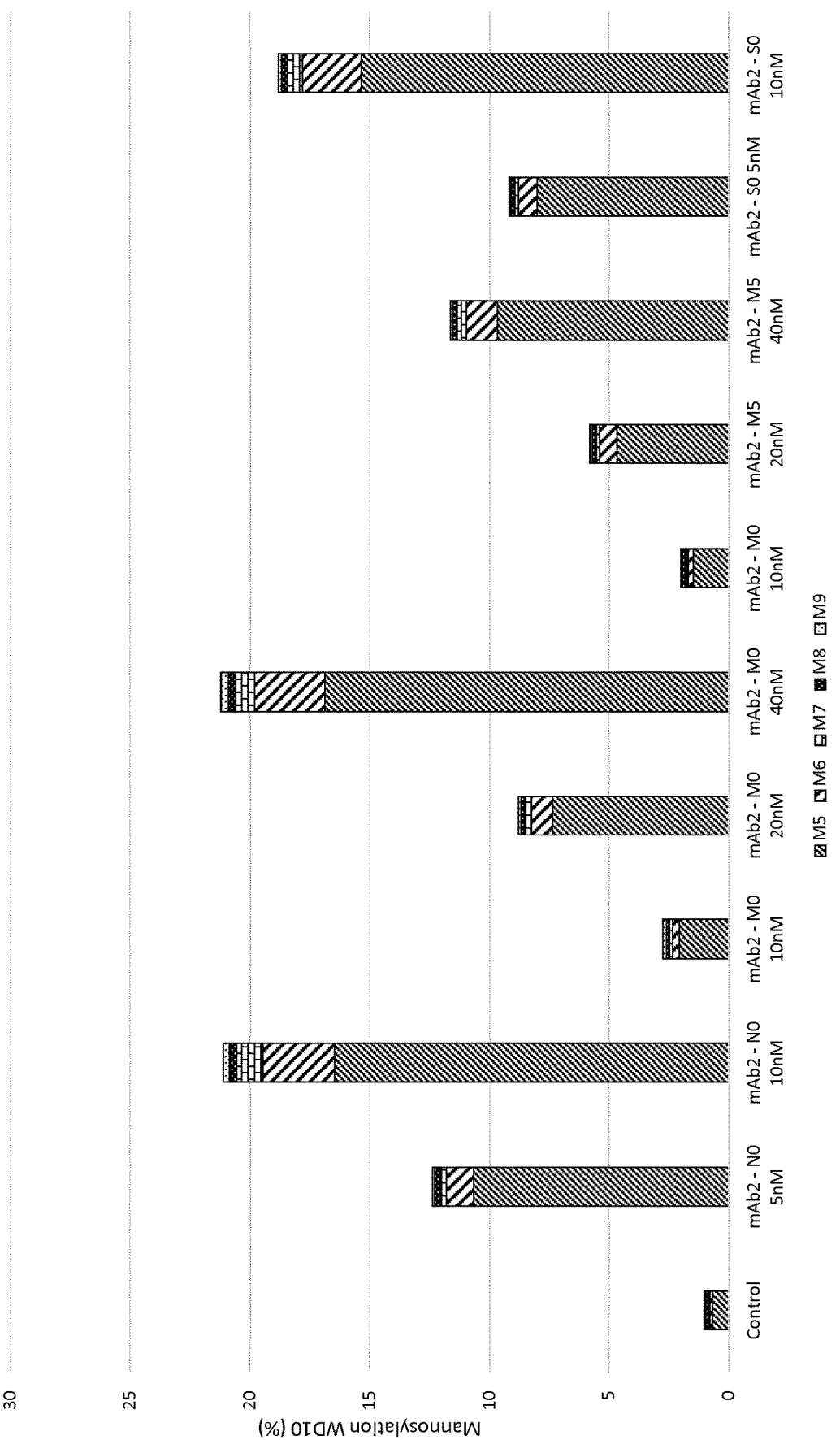
FIG. 11 shows the mannosylation profile at day 10 (FIG. 11A) and day 12 (FIG. 11B) for mAb2 cultured at different polyether ionophores concentrations in minibioreactor Ambr. Results are presented as mean±standard deviation.
Figure 11B:
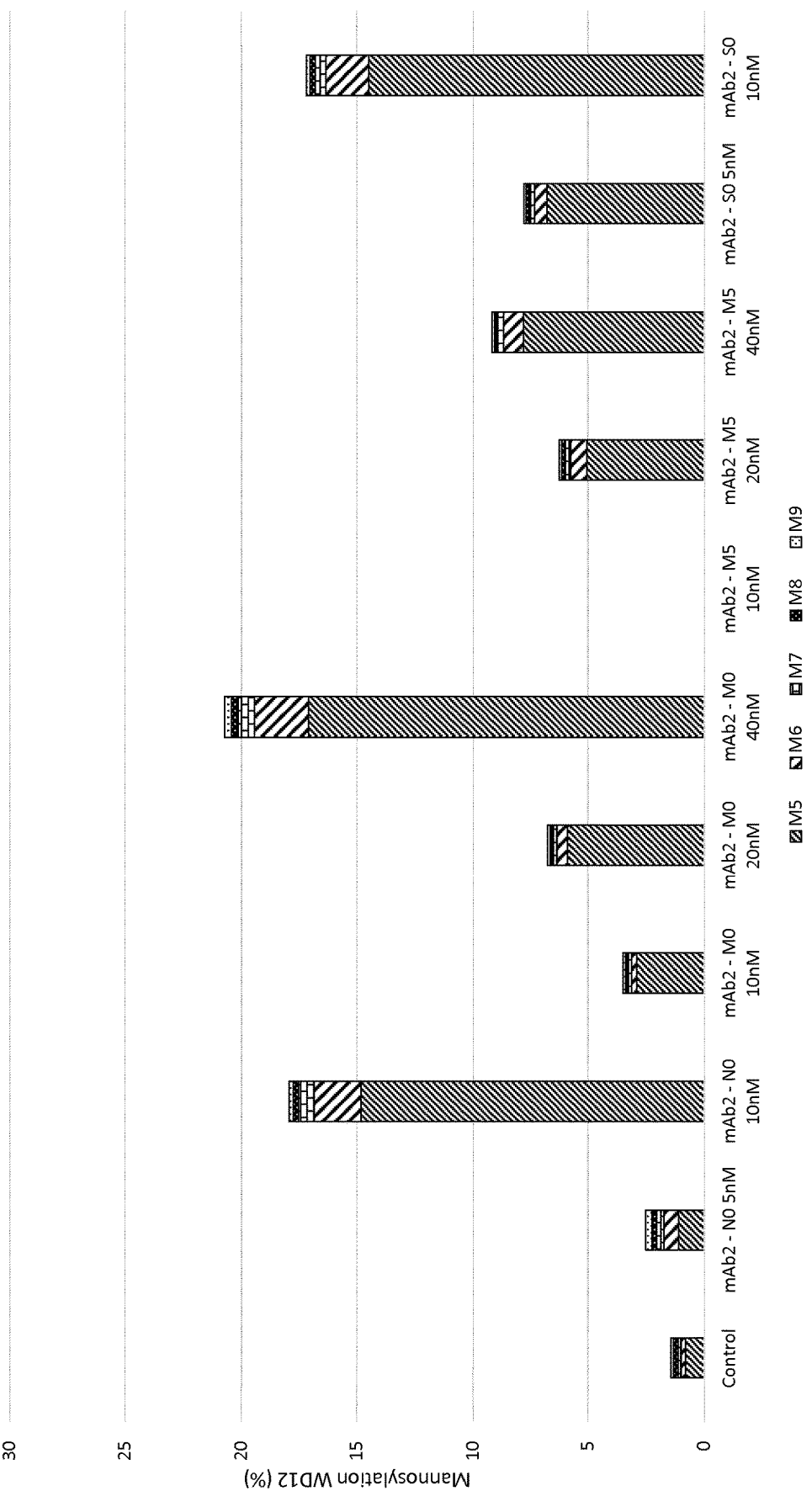

Glycosylation Profiles:

Glycosylation profiles are shown on FIG. 11 (FIG. 11A at day 10 and FIG. 11B at day 12). The data obtained underlined that:

For polyether ionophores added at the start of the culture, the data obtained underlines that:

The polyether ionophores narasin, salinomycin and maduramycin have a strong impact on the mannosylation level of mAb2, compared to the control, especially on Man5 species. For example, at day 10 the level of Man5 species increased from about 0.7% (for the control) to up to about 15% with 10 mM of salinomycin and up to about 16.5% for both 40 mM maduramycin and 10 mM narasin.

The polyether ionophores narasin, salinomycin and maduramycin have also an impact, although to a lesser extent on the Man6-Man9 species level of mAb2, compared to the control. For example, at day 10:

The level of Man6 species (M6) increased from about 0.1% (for the control) to up to about 2.5% with 10 mM of salinomycin and up to about 3% for both 40 mM maduramycin and 10 mM narasin.

The level of Man7 species increased from about 0.05% (for the control) to up to about 0.65% with 10 mM salinomycin, up to about 0.8% with 40 mM maduramycin or up to about 1.0% with 10 mM narasin.

As seen for mAb1, the impact on the total mannosylation level varies a lot as a function of the polyether ionophore that is used. Once more, when comparing the effect of salinomycin, narasin and maduramycin at 10 nM, narasin showed the highest mannosylation increase. Indeed using 10 nM narasin, the total mannosylation reached about 12.0% after 10 days of culture and 18.0% after 12 days of culture. On the contrary, maduramycin had the lowest effect on mannosylation with total mannosylation of 2.7% after 10 days of culture and about 3.5% after 12 days of culture.

The impact on the mannosylation level of mAb2, compared to the control, can be modulated as a function of the nature/concentration of the polyether ionophore that is used and the elapsed time in culture (10 or 12 days for example).

For polyether ionophores added as feed during the culture, the data obtained underlined that:
  Addition of the compound (such as maduramycin) also impact the mannosylation level.
  The main impact is once more mainly on the Man5 species, however a unneglectable effect has been shown on Man6 and Man7, especially at the highest concentrations tested.

Conclusion for mAb2:

The present results surprisingly underline that salinomycin, narasin and maduramycin are able to modulate the mannosylation of an Fc-fusion protein, here mAb2, and in particular are able to deeply increase the amount of Man5 species, and to a lesser extend M6 to M9, without deeply impacting afucoslyated glycoforms (data non shown). Although not shown, the level of fucosylated glycoforms decreased while Man glycoforms increased. This example shows that the mannosylation can be fine-tune based on the teaching of the present invention by playing with the nature/concentration of the polyether ionophore that is used (salinomycin, narasin or maduramycin), the elapsed time in culture and the timing of addition of the molecule, i.e. at the start of the culture (such as in the cell culture before or just after seeding), or as a feed at a later stage (e.g. day 5 in example 3).

Overall Conclusions

The present examples demonstrate that the polyether ionophores salinomycin, narasin and maduramycin specifically modulate mannosylation by increasing the high mannose species, while decreasing fucosylated species. The skilled person will understand from the results of the above examples that he can use any one of salinomycin, narasin and maduramycin for modulating the mannosylation profile of any antibodies and any proteins, whatever the cell line that is used for production, and in particular to increase the overall mannosylation level. Both additions at the start of the culture and as feed proofed to be excellent strategies to modulate mannosylation levels. It was also surprisingly found that another polyether ionophore, lasalocid, had no impact on mannosylation.

The exact concentration of any one of salinomycin, narasin and maduramycin to be added in the cell culture media, as well as the timing for addition/supplementation (either at the start of the culture or as feed(s) at later points in time) will have to be determined case by case, depending on the mannosylation profile the skilled one wishes to obtain molecule per molecule. This determination can be done without involving any inventive skill, based on the teaching of the present invention. The skilled person will also understand that he can use any one of salinomycin, narasin and maduramycin in any method for producing a protein such as an antibody, even if he does not aim to reach a particular glycosylation profile.

TABLE 2

Conditions tested on mAb1 and mAb2 to modulate mannosylation

| Concentration (nM) | Compound | | | | |
| --- | --- | --- | --- | --- | --- |
| | Narasin (mAb1 and mAb2) | Salinomycin (mAb1 and mAb2) | Maduramycin (mAb1) | Maduramycin (mAb2) | Addition day |
| Concentration 1 (nM) | 5 | 5 | 10 | 10 | 0 |
| Concentration 2 (nM) | 10 | 10 | 20 | 20 | 0 |
| Concentration 3 (nM) | | | 40 | 40 | 0 |
| Concentration 4 (nM) | | | 10 | | 7 |
| Concentration 5 (nM) | | | 20 | | 7 |
| Concentration 6 (nM) | | | 40 | | 7 |
| Concentration 7 (nM) | | | | 10 | 5 |
| Concentration 8 (nM) | | | | 20 | 5 |
| Concentration 9 (nM) | | | | 40 | 5 |

REFERENCES

1) Eon-Duval et al., 2012. Quality Attributes of Recombinant Therapeutic Proteins: An Assessment of Impact on Safety and Efficacy as Part of a Quality by Design Development Approach. Biotechnol. Prog. 28(3): 608-622.

2) N. Yamane-Ohnuki et M. Satoh, 2009. Production of therapeutic antibodies with controlled fucosylation; mAbs, 1(3): 230-236.

3) Yu et al., 2012. Characterization and pharmacokinetic properties of antibodies with N-linked Mannose-5 glycans"; mAbs, 4(4):475-487.

4) Ziv Roth et al., 2012. Identification and Quantification of Protein Glycosylation; International Journal of Carbohydrate Chemistry, Article ID 640923.

5) Ting Song et al., 2014. In-Depth Method for the Characterization of Glycosylation in Manufactured Recombinant Monoclonal Antibody Drugs; Anal. Chem., 86(12): 5661-5666.

6) Varki et al., 1999, Essentials of Glycobiology, Cold Spring Harbor Lab Press.

7) Voisard et al., 2003, Biotechnol. Bioeng. 82:751-765.

8) Ausubel et al., 1988 and updates, Current Protocols in Molecular Biology, eds. Wiley & Sons, New York.

9) Sambrook et al., 1989 and updates, Molecular Cloning: A Laboratory Manual, Cold Spring Laboratory Press.

10) Remington's Pharmaceutical Sciences, 1995, 18th ed., Mack Publishing Company, Easton, Pa.

The invention claimed is:

1. A method of producing a recombinant protein with a modulated mannosylation profile, said method comprising culturing a host cell expressing said protein in cell culture medium comprising a polyether ionophore, wherein the host cell is a Chinese Hamster Ovary (CHO) cell and wherein the polyether ionophore is selected from the group consisting of maduramycin, narasin and salinomycin.

2. The method according to claim 1, wherein the modulation of the mannosylation level is an increase in the mannosylation level in said protein.

3. The method according to claim 1, further comprising purifying said recombinant protein with a modulated mannosylation profile.

4. The method according to claim 1, wherein the recombinant protein is selected from the group consisting of an antibody or antigen binding fragment thereof, a human antibody or antigen-binding portion thereof, a humanized antibody or antigen-binding portion thereof, a chimeric antibody or antigen-binding portion thereof, a fusion protein, a growth factor, a hormone, and a cytokine.

5. The method according to claim 1, wherein the concentration of polyether ionophore in the cell culture medium is about 0.5 nM to 250 nM.

6. The method according to claim 5, wherein the concentration of the polyether ionophore is 1 nM to 200 nM.

7. A method of producing a recombinant protein with a modulated mannosylation profile, said method comprising culturing a host cell expressing said protein in cell culture medium complemented with at least one feed comprising a polyether ionophore wherein the host cell is a Chinese Hamster Ovary (CHO) cell and wherein the polyether ionophore is selected from the group consisting of maduramycin, narasin and salinomycin.

8. The method according to claim 7, wherein the recombinant protein is selected from the group consisting of an antibody or antigen binding fragment thereof, a human antibody or antigen-binding portion thereof, a humanized antibody or antigen-binding portion thereof, a chimeric antibody or antigen-binding portion thereof, a fusion protein, a growth factor, a hormone and a cytokine.

9. The method according to claim 7, wherein the concentration of polyether ionophore in the cell culture medium is about 0.5 nM to 250 nM.

10. The method according to claim 9, wherein the concentration of the polyether ionophore is 1 nM to 200 nM.

* * * * *

UNITED STATES PATENT AND TRADEMARK OFFICE
CERTIFICATE OF CORRECTION

PATENT NO. : 11,566,062 B2
APPLICATION NO. : 16/954544
DATED : January 31, 2023
INVENTOR(S) : David Bruhlmann et al.

Page 1 of 2

It is certified that error appears in the above-identified patent and that said Letters Patent is hereby corrected as shown below:

In the Specification

Column 1,
Line 41, "FcyRllla" should read --FcγRIIIa--.

Column 2,
Line 43, "SO followed" should read --S0 followed--.
Line 45, "NO followed" should read --N0 followed--.
Line 46, "MO followed" should read --M0 followed--.

Column 9,
Lines 25-31, " 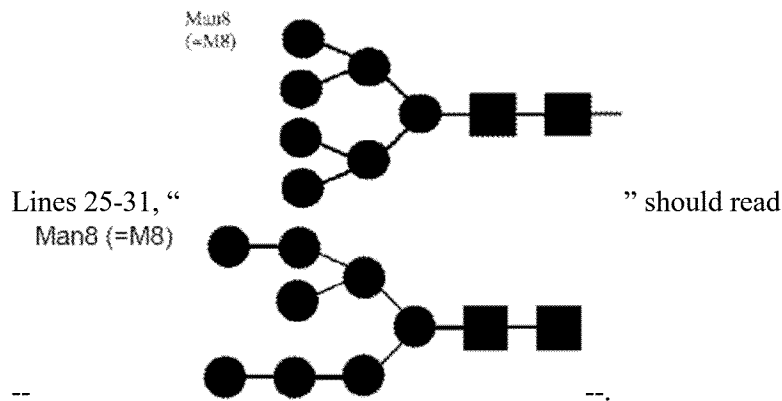 " should read
-- --.

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 11,566,062 B2

Column 10,

Lines 14-25, " 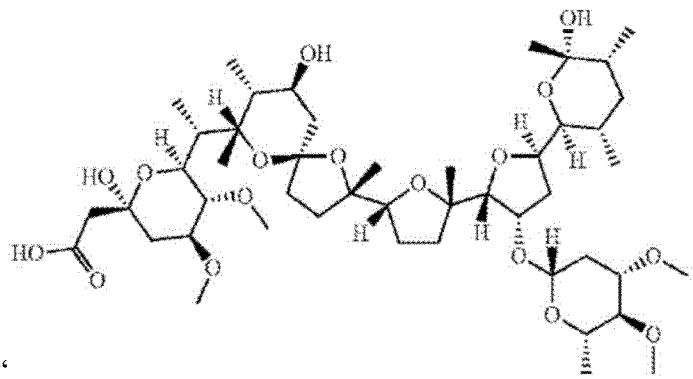 " should read

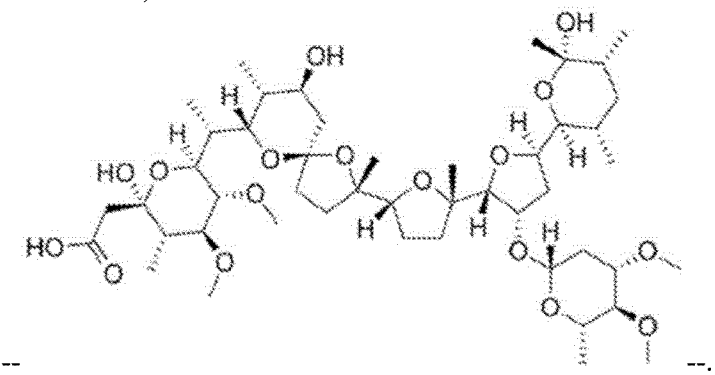

--      --.

Column 11,

Lines 5-10, " 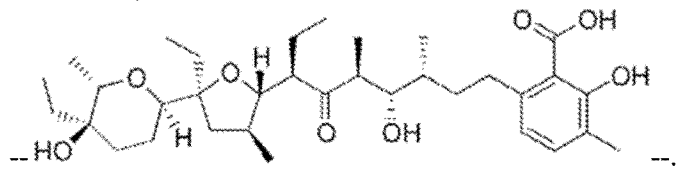 " should read

-- -- .

Column 12,
Line 2, "Mang," should read --Man8,--.

Column 16,
Line 57, "ManS" should read --Man5--.
Line 58, "ManS" should read --Man5--.